(12) United States Patent
Mastroianni et al.

(10) Patent No.: US 7,981,602 B2
(45) Date of Patent: Jul. 19, 2011

(54) PHOTOPROTEINS WITH ENHANCED BIOLUMINESCENCE AND ASSAYS USING THE SAME

(75) Inventors: Nadia Mastroianni, Milan (IT); Silvia Cainarca, Milan (IT); Sabrina Corazza, Milan (IT)

(73) Assignee: AXXAM S.R.L., Milan (IT)

( * ) Notice: Subject to any disclaimer, the term of this patent is extended or adjusted under 35 U.S.C. 154(b) by 898 days.

(21) Appl. No.: 10/587,523

(22) PCT Filed: Mar. 9, 2006

(86) PCT No.: PCT/EP2006/002172
§ 371 (c)(1),
(2), (4) Date: Mar. 7, 2007

(87) PCT Pub. No.: WO2006/094805
PCT Pub. Date: Sep. 14, 2006

(65) Prior Publication Data
US 2007/0259389 A1    Nov. 8, 2007

(30) Foreign Application Priority Data

Mar. 11, 2005  (EP) .................................... 05005390
Jan. 5, 2006   (EP) .................................... 06000171

(51) Int. Cl.
*C07K 14/435* (2006.01)
*C12N 15/12* (2006.01)
*C12Q 1/66* (2006.01)

(52) U.S. Cl. ........ 435/6; 530/350; 536/23.5; 435/320.1; 435/252.3; 435/325

(58) Field of Classification Search .................. None
See application file for complete search history.

(56) References Cited

U.S. PATENT DOCUMENTS 5,360,728 A * 11/1994 Prasher .................... 435/189
2005/0130262 A1* 6/2005 Lambolez et al. ........... 435/69.1

FOREIGN PATENT DOCUMENTS

WO    03/006497   *  1/2003

OTHER PUBLICATIONS

K. Tsuzuki et al. "Thermostable Mutants of the Photoprotein Aequorin Obtained by in Vitro Evolution", J. Biol. Chem. 280(40: 34324-34331. (Jun. 2005).*

* cited by examiner

*Primary Examiner* — Rebecca Prouty
(74) *Attorney, Agent, or Firm* — Arent Fox, LLP

(57) ABSTRACT

The present invention relates to photoproteins with enhanced bioluminescence obtained by mutagenesis of clytin, to their use as intracellular calcium indicators and in cell-based assays.

16 Claims, 16 Drawing Sheets

SEQUENCE LISTING

<160> NUMBER OF SEQ ID NOS: 24

<210> SEQ ID NO 1
<211> LENGTH: 198
<212> TYPE: PRT
<213> ORGANISM: Clytia gregaria

<400> SEQUENCE: 1

Met Ala Asp Thr Ala Ser Lys Tyr Ala Val Lys Leu Arg Pro Asn Phe
1               5                   10                  15

Asp Asn Pro Lys Trp Val Asn Arg His Lys Phe Met Phe Asn Phe Leu
            20                  25                  30

Asp Ile Asn Gly Asp Gly Lys Ile Thr Leu Asp Glu Ile Val Ser Lys
        35                  40                  45

Ala Ser Asp Asp Ile Cys Ala Lys Leu Gly Ala Thr Pro Glu Gln Thr

```
                50                  55                  60
Lys Arg His Gln Asp Ala Val Glu Ala Phe Phe Lys Lys Ile Gly Met
 65                  70                  75                  80

Asp Tyr Gly Lys Glu Val Glu Phe Pro Ala Phe Val Asp Gly Trp Lys
                 85                  90                  95

Glu Leu Ala Asn Tyr Asp Leu Lys Leu Trp Ser Gln Asn Lys Lys Ser
                100                 105                 110

Leu Ile Arg Asp Trp Gly Glu Ala Val Phe Asp Ile Phe Asp Lys Asp
                115                 120                 125

Gly Ser Gly Ser Ile Ser Leu Asp Glu Trp Lys Ala Tyr Gly Arg Ile
130                 135                 140

Ser Gly Ile Cys Ser Ser Asp Glu Asp Ala Glu Lys Thr Phe Lys His
145                 150                 155                 160

Cys Asp Leu Asp Asn Ser Gly Lys Leu Asp Val Asp Glu Met Thr Arg
                165                 170                 175

Gln His Leu Gly Phe Trp Tyr Thr Leu Asp Pro Asn Ala Asp Gly Leu
                180                 185                 190

Tyr Gly Asn Phe Val Pro
        195

<210> SEQ ID NO 2
<211> LENGTH: 198
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 2

Met Ala Asp Thr Ala Ser Lys Tyr Ala Val Lys Leu Arg Pro Asn Phe
  1               5                  10                  15

Asp Asn Pro Lys Trp Val Asn Arg His Lys Phe Met Phe Asn Phe Leu
                 20                  25                  30

Asp Ile Asn Gly Asp Gly Lys Ile Thr Leu Asp Glu Ile Val Ser Lys
             35                  40                  45

Ala Ser Asp Asp Ile Ser Ala Lys Leu Gly Ala Thr Pro Glu Gln Thr
 50                  55                  60

Lys Arg His Gln Asp Ala Val Glu Ala Phe Phe Lys Lys Ile Gly Met
 65                  70                  75                  80

Asp Tyr Gly Lys Glu Val Glu Phe Pro Ala Phe Val Asp Gly Trp Lys
                 85                  90                  95

Glu Leu Ala Asn Tyr Asp Leu Lys Leu Trp Ser Gln Asn Lys Lys Ser
                100                 105                 110

Leu Ile Arg Asp Trp Gly Glu Ala Val Phe Asp Ile Phe Asp Lys Asp
                115                 120                 125

Gly Ser Gly Ser Ile Ser Leu Asp Glu Trp Lys Ala Tyr Gly Arg Ile
130                 135                 140

Ser Gly Ile Cys Ser Ser Asp Glu Asp Ala Glu Lys Thr Phe Lys His
145                 150                 155                 160

Cys Asp Leu Asp Asn Ser Gly Lys Leu Asp Val Asp Glu Met Thr Arg
                165                 170                 175

Gln His Leu Gly Phe Trp Tyr Thr Leu Asp Pro Asn Ala Asp Gly Leu
                180                 185                 190

Tyr Gly Asn Phe Val Pro
        195
```

-continued

```
<210> SEQ ID NO 3
<211> LENGTH: 198
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 3

Met Ala Asp Thr Ala Ser Lys Tyr Ala Val Lys Leu Arg Pro Asn Phe
 1               5                  10                  15

Asp Asn Pro Lys Trp Val Asn Arg His Lys Phe Met Phe Asn Phe Leu
            20                  25                  30

Asp Ile Asn Gly Asp Gly Lys Ile Thr Leu Asp Glu Ile Val Ser Lys
        35                  40                  45

Ala Ser Asp Asp Ile Cys Ala Lys Leu Gly Ala Thr Pro Glu Gln Thr
    50                  55                  60

Lys Arg His Gln Asp Ala Val Glu Ala Phe Phe Lys Lys Ile Gly Met
65                  70                  75                  80

Asp Tyr Gly Lys Glu Val Glu Phe Pro Ala Phe Val Asp Gly Trp Lys
                85                  90                  95

Glu Leu Ala Asn Tyr Asp Leu Lys Leu Trp Ser Gln Asn Lys Lys Ser
            100                 105                 110

Leu Ile Arg Asp Trp Gly Glu Val Phe Asp Ile Phe Asp Lys Asp
        115                 120                 125

Gly Ser Gly Cys Ile Ser Leu Asp Glu Trp Lys Ala Tyr Gly Arg Ile
    130                 135                 140

Ser Gly Ile Cys Ser Ser Asp Glu Asp Ala Glu Lys Thr Phe Lys His
145                 150                 155                 160

Cys Asp Leu Asp Asn Ser Gly Lys Leu Asp Val Asp Glu Met Thr Arg
                165                 170                 175

Gln His Leu Gly Phe Trp Tyr Thr Leu Asp Pro Asn Ala Asp Gly Leu
            180                 185                 190

Tyr Gly Asn Phe Val Pro
        195

<210> SEQ ID NO 4
<211> LENGTH: 198
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 4

Met Ala Asp Thr Ala Ser Lys Tyr Ala Val Lys Leu Arg Pro Asn Phe
 1               5                  10                  15

Asp Asn Pro Lys Trp Val Asn Arg His Lys Phe Met Phe Asn Phe Leu
            20                  25                  30

Asp Ile Asn Gly Asp Gly Lys Ile Thr Leu Asp Glu Ile Val Ser Arg
        35                  40                  45

Ala Ser Asp Asp Ile Cys Ala Lys Leu Gly Ala Thr Pro Glu Gln Thr
    50                  55                  60

Lys Arg His Gln Asp Ala Val Glu Ala Phe Phe Lys Lys Ile Gly Met
65                  70                  75                  80

Asp Tyr Gly Lys Glu Val Glu Phe Pro Ala Phe Val Asp Gly Trp Lys
                85                  90                  95

Glu Leu Ala Asn Tyr Asp Leu Lys Leu Trp Ser Gln Asn Lys Lys Ser
            100                 105                 110
```

```
Leu Ile Arg Asp Trp Gly Glu Ala Val Phe Asp Ile Phe Asp Lys Asp
            115                 120                 125

Gly Ser Gly Ser Ile Ser Leu Asp Glu Trp Lys Ala Tyr Gly Arg Ile
        130                 135                 140

Ser Gly Ile Cys Ser Ser Asp Glu Asp Ala Glu Lys Thr Phe Lys His
145                 150                 155                 160

Cys Asp Leu Asp Asn Ser Gly Lys Leu Asp Val Asp Glu Met Thr Arg
                165                 170                 175

Gln His Leu Gly Phe Trp Tyr Thr Leu Asp Pro Asn Ala Asp Gly Leu
            180                 185                 190

Tyr Gly Asp Phe Val Pro
            195
```

<210> SEQ ID NO 5
<211> LENGTH: 198
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 5

```
Met Ala Asp Thr Ala Ser Lys Tyr Ala Val Lys Leu Arg Pro Asn Phe
 1               5                  10                  15

Asp Asn Pro Lys Trp Val Asn Arg His Lys Phe Met Phe Asn Phe Leu
                20                  25                  30

Asp Ile Asn Gly Asp Gly Lys Ile Thr Leu Asp Glu Ile Val Ser Lys
            35                  40                  45

Ala Ser Asp Asp Ile Cys Ala Lys Leu Gly Ala Thr Pro Glu Gln Thr
        50                  55                  60

Lys Arg His Arg Asp Ala Val Glu Ala Phe Phe Lys Lys Ile Gly Met
65                  70                  75                  80

Asp Tyr Gly Lys Glu Val Glu Phe Pro Val Phe Val Asp Gly Trp Lys
                85                  90                  95

Glu Leu Ala Asn Tyr Asp Leu Lys Leu Trp Ser Gln Asn Lys Lys Ser
            100                 105                 110

Leu Ile Arg Asp Trp Gly Glu Ala Val Phe Asp Ile Phe Asp Lys Asp
        115                 120                 125

Gly Ser Gly Ser Ile Ser Leu Asp Glu Trp Lys Ala Tyr Gly Arg Ile
    130                 135                 140

Ser Gly Ile Cys Ser Ser Asp Glu Asp Ala Glu Lys Thr Phe Lys His
145                 150                 155                 160

Cys Asp Leu Asp Asn Ser Gly Lys Leu Asp Val Asp Glu Met Thr Arg
                165                 170                 175

Gln His Leu Gly Phe Trp Tyr Ile Leu Asp Pro Asn Ala Asp Gly Leu
            180                 185                 190

Tyr Gly Asn Phe Val Pro
            195
```

<210> SEQ ID NO 6
<211> LENGTH: 198
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 6

```
Met Ala Asp Thr Ala Ser Lys Tyr Ala Val Lys Leu Arg Pro Asn Phe
  1               5                  10                  15

Asp Asn Pro Lys Trp Val Asn Arg His Lys Phe Met Phe Asn Phe Leu
             20                  25                  30

Asp Ile Asn Gly Asp Gly Lys Ile Thr Leu Asp Glu Ile Val Ser Lys
         35                  40                  45

Ala Ser Asp Asp Ile Cys Ala Lys Leu Gly Ala Thr Pro Glu Gln Thr
     50                  55                  60

Lys Arg His Gln Asp Ala Val Glu Ala Phe Phe Lys Lys Ile Gly Met
 65              70                  75                  80

Asp Phe Gly Lys Glu Val Glu Phe Pro Ala Phe Val Asp Gly Trp Lys
             85                  90                  95

Glu Leu Ala Asn Tyr Asp Leu Lys Leu Trp Ser Gln Asn Asn Lys Ser
            100                 105                 110

Leu Ile Arg Asp Trp Gly Glu Ala Val Phe Asp Ile Leu Asp Lys Asp
        115                 120                 125

Gly Ser Gly Ser Ile Ser Leu Asp Glu Trp Lys Ala Tyr Gly Arg Ile
    130                 135                 140

Ser Gly Ile Cys Arg Ser Asp Glu Asp Ala Glu Lys Thr Phe Lys His
145                 150                 155                 160

Cys Asp Leu Asp Asn Ser Gly Lys Leu Asp Val Asp Glu Met Thr Arg
                165                 170                 175

Gln His Leu Gly Phe Trp Tyr Thr Leu Asp Pro Asn Ala Asp Gly Leu
            180                 185                 190

Tyr Gly Asn Phe Val Pro
            195

<210> SEQ ID NO 7
<211> LENGTH: 198
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 7

Met Ala Asp Thr Ala Ser Lys Tyr Ala Val Lys Leu Arg Pro Asn Phe
  1               5                  10                  15

Asp Asn Pro Lys Trp Val Asn Arg His Lys Phe Met Phe Asn Phe Leu
             20                  25                  30

Asp Ile Asn Gly Asp Gly Lys Ile Thr Leu Asp Glu Ile Val Ser Lys
         35                  40                  45

Ala Ser Asp Asp Ile Cys Ala Lys Leu Gly Ala Thr Pro Glu Gln Thr
     50                  55                  60

Lys Arg His Gln Asp Ala Val Glu Ala Phe Phe Lys Lys Ile Gly Met
 65              70                  75                  80

Asp Tyr Gly Lys Glu Val Glu Phe Pro Ala Phe Val Asp Gly Trp Lys
             85                  90                  95

Glu Leu Ala Asn Tyr Asp Leu Lys Leu Trp Ser Gln Asn Lys Lys Ser
            100                 105                 110

Leu Ile Arg Asp Trp Gly Glu Ala Val Phe Asp Ile Phe Asp Lys Asp
        115                 120                 125

Gly Ser Gly Ser Ile Ser Leu Asp Glu Trp Lys Ala Tyr Cys Arg Ile
    130                 135                 140

Ser Gly Ile Cys Ser Ser Asp Glu Asp Ala Glu Lys Thr Phe Lys His
145                 150                 155                 160
```

```
Cys Asp Leu Asp Asn Ser Gly Lys Leu Asp Val Asp Glu Met Thr Arg
            165                 170                 175

Gln His Leu Gly Phe Trp Tyr Thr Leu Asp Pro Asn Ala Asp Gly Leu
            180                 185                 190

Tyr Gly Asn Phe Val Pro
        195

<210> SEQ ID NO 8
<211> LENGTH: 198
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 8

Met Ala Asp Thr Ala Ser Lys Tyr Ala Val Lys Leu Arg Pro Asn Phe
  1               5                  10                  15

Asp Asn Pro Lys Trp Val Asn Arg His Lys Phe Met Phe Asn Phe Leu
            20                  25                  30

Asp Ile Asn Gly Asp Gly Lys Ile Thr Leu Asp Glu Ile Val Ser Lys
        35                  40                  45

Ala Ser Asp Asp Val Cys Ala Lys Leu Gly Ala Thr Pro Glu Gln Thr
    50                  55                  60

Lys Arg His Gln Asp Ala Val Glu Ala Phe Phe Lys Lys Ile Gly Met
 65                  70                  75                  80

Asp Tyr Gly Lys Glu Val Glu Phe Pro Ala Phe Val Asp Gly Trp Lys
                85                  90                  95

Glu Leu Ala Asn Tyr Asp Leu Lys Leu Trp Ser Gln Asn Lys Lys Ser
            100                 105                 110

Leu Ile Arg Asp Trp Gly Glu Ala Val Phe Asp Ile Phe Asp Lys Asp
        115                 120                 125

Gly Ser Gly Ser Ile Ser Leu Asp Glu Trp Lys Ala Tyr Gly Arg Ile
    130                 135                 140

Ser Gly Ile Cys Arg Ser Asp Glu Asp Ala Glu Lys Thr Phe Lys His
145                 150                 155                 160

Cys Asp Leu Asp Asn Ser Gly Lys Leu Asp Val Asp Glu Met Thr Arg
            165                 170                 175

Gln His Leu Gly Phe Trp Tyr Thr Leu Asp Pro Asn Ala Asp Gly Leu
            180                 185                 190

Tyr Gly Asn Phe Val Pro
        195

<210> SEQ ID NO 9
<211> LENGTH: 198
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 9

Met Ala Asp Thr Ala Ser Lys Tyr Ala Val Lys Leu Arg Pro Asn Phe
  1               5                  10                  15

Asp Asp Pro Lys Trp Val Asn Arg His Lys Phe Met Phe Asn Phe Leu
            20                  25                  30

Asp Ile Asn Gly Asp Gly Lys Val Thr Leu Asp Glu Ile Val Ser Lys
        35                  40                  45

Ala Ser Asp Asp Ile Cys Ala Arg Leu Gly Ala Thr Pro Glu Gln Thr
```

```
                50                   55                   60
Lys Arg His Gln Asp Ala Val Glu Ala Phe Phe Lys Lys Ile Gly Met
 65                   70                   75                   80

Asp Tyr Gly Lys Glu Val Glu Phe Pro Ala Phe Val Asp Gly Trp Lys
                 85                   90                   95

Glu Leu Ala Asn Tyr Asp Leu Lys Leu Trp Ser Gln Asn Lys Lys Ser
                100                  105                  110

Leu Ile Arg Asp Trp Gly Glu Ala Val Phe Asp Ile Phe Asp Lys Asp
                115                  120                  125

Gly Ser Gly Ser Ile Ser Leu Asp Glu Trp Lys Ala Tyr Gly Arg Ile
                130                  135                  140

Ser Gly Ile Cys Ser Ser Asp Glu Asp Ala Glu Lys Thr Phe Lys His
145                  150                  155                  160

Cys Asp Leu Asp Asn Ser Gly Lys Leu Asp Val Asp Glu Met Thr Arg
                165                  170                  175

Gln His Leu Gly Phe Trp Tyr Thr Leu Asp Pro Asn Ala Asp Gly Leu
                180                  185                  190

Tyr Gly Asn Phe Val Pro
            195

<210> SEQ ID NO 10
<211> LENGTH: 198
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 10

Met Ala Asp Thr Ala Ser Lys Tyr Ala Val Lys Leu Arg Pro Asn Phe
  1               5                   10                  15

Asp Asn Pro Lys Trp Val Asn Arg His Lys Phe Met Phe Asn Phe Leu
                 20                   25                   30

Asp Ile Asn Gly Asp Gly Lys Ile Thr Leu Asp Glu Ile Val Ser Lys
                 35                   40                   45

Ala Ser Asp Asp Ile Cys Ala Lys Leu Glu Ala Thr Pro Glu Gln Thr
 50                   55                   60

Lys Arg His Gln Val Cys Val Glu Ala Phe Phe Arg Gly Cys Gly Met
 65                   70                   75                   80

Glu Tyr Gly Lys Glu Ile Ala Phe Pro Gln Phe Leu Asp Gly Trp Lys
                 85                   90                   95

Gln Leu Ala Thr Ser Glu Leu Lys Lys Trp Ala Arg Asn Glu Pro Thr
                100                  105                  110

Leu Ile Arg Glu Trp Gly Asp Ala Val Phe Asp Ile Phe Asp Lys Asp
                115                  120                  125

Gly Ser Gly Ser Ile Ser Leu Asp Glu Trp Lys Ala Tyr Gly Arg Ile
                130                  135                  140

Ser Gly Ile Cys Ser Ser Asp Glu Asp Ala Glu Lys Thr Phe Lys His
145                  150                  155                  160

Cys Asp Leu Asp Asn Ser Gly Lys Leu Asp Val Asp Glu Met Thr Arg
                165                  170                  175

Gln His Leu Gly Phe Trp Tyr Thr Leu Asp Pro Asn Ala Asp Gly Leu
                180                  185                  190

Tyr Gly Asn Phe Val Pro
            195
```

<210> SEQ ID NO 11
<211> LENGTH: 600
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 11

```
atggccgaca ccgccagcaa gtacgccgtg aagctgaggc ccaacttcga caaccccaag      60
tgggtgaacc ggcacaagtt catgttcaac ttcctggaca tcaacggcga cggcaagatc     120
accctggacg agatcgtgag caaggccagc gacgacatct gcgccaagct gggcgccacc     180
cccgagcaga ccaagagaca ccaggacgcc gtggaggcct tcttcaagaa gatcggcatg     240
gactacggca aggaggtgga gttccccgcc ttcgtggacg gctggaagga gctggccaac     300
taccacctga agctgtggag ccagaacaag aagagcctca tcagggactg gggcgaggcc     360
gtgttcgaca tcttcgacaa ggacggcagc ggctgcatca gcctggatga gtggaaggcc     420
tacggcagaa tcagcggcat ctgcagcagc gacgaggacg ccgaaaagac cttcaagcac     480
tgcgacctgg acaacagcgg caagctggac gtggacgaga tgaccagaca gcacctggac     540
ttctggtaca ccctggaccc caatgccgac ggcctgtacg caacttcgt gccttgataa      600
```

<210> SEQ ID NO 12
<211> LENGTH: 600
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 12

```
atggccgaca ccgccagcaa gtacgccgtg aagctgaggc ccaacttcga caaccccaag      60
tgggtgaacc ggcacaagtt catgttcaac ttcctggaca tcaacggcga cggcaagatc     120
accctggacg agatcgtgag caaggccagc gacgacatct gcgccaagct gggcgccacc     180
cccgagcaga ccaagagaca ccaggacgcc gtggaggcct tcttcaagaa gatcggcatg     240
gactacggca aggaggtgga gttccccgcc ttcgtggacg gctggaagga gctggccaac     300
tacgacctga agctgtggag ccagaacaag aagagcctca tcagggactg gggcgaggcc     360
gtgttcgaca tcttcgacaa ggacggcagc ggctgcatca gcctggatga gtggaaggcc     420
tacggcagaa tcagcggcat ctgcagcagc gacgaggacg ccgaaaagac cttcaagcac     480
tgcgacctgg acaacagcgg caagctggac gtggacgaga tgaccagaca gcacctgggc     540
ttctggtaca ccctggaccc caatgccgac ggcctgtacg caacttcgt gccttgataa      600
```

<210> SEQ ID NO 13
<211> LENGTH: 600
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 13

```
atggccgaca ccgccagcaa gtacgccgtg aagctgaggc ccaacttcga caaccccaag      60
tgggtgaacc ggcacaagtt catgttcaac ttcctggaca tcaacggcga cggcaagatc     120
accctggacg agatcgtgag cagggccagc gacgacatct gcgccaagct gggcgccacc     180
cccgagcaga ccaagagaca ccaggacgcc gtggaggcct tcttcaagaa gatcggcatg     240
```

```
gactacggca aggaggtgga gttccccgcc ttcgtggacg gctggaagga gctggccaac    300
tacgacctga agctgtggag ccagaacaag aagagcctca tcagggactg gggcgaggcc    360
gtgttcgaca tcttcgacaa ggacggcagc ggcagcatca gcctggatga gtggaaggcc    420
tacggcagaa tcagcggcat ctgcagcagc gacgaggacg ccgaaaagac cttcaagcac    480
tgcgacctgg acaacagcgg caagctggac gtggacgaga tgaccagaca gcacctgggc    540
ttctggtaca ccctggaccc caacgccgac ggcctgtacg gcgacttcgt gccttgataa    600
```

<210> SEQ ID NO 14
<211> LENGTH: 600
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 14

```
atggccgaca ccgccagcaa gtacgccgtg aagctgaggc ccaacttcga caaccccaag     60
tgggtgaacc ggcacaagtt catgttcaat ttcctggaca tcaacggcga cggcaagatc    120
accctggacg agatcgtgag caaggccagc gacgacatct gcgccaagct gggcgccacc    180
cccgagcaga ccaagagaca ccgggacgcc gtggaggcct tcttcaagaa gatcggcatg    240
gactacggca aggaggtgga gttccccgtc ttcgtggacg gctggaagga gctggccaac    300
tacgacctga agctgtggag ccagaacaag aagagcctca tcagggactg gggcgaggcc    360
gtgtttgaca tcttcgacaa ggacggcagc ggcagcatta gcctggatga gtggaaggcc    420
tacggtagaa tcagcggcat ctgcagcagc gacgaggacg ccgaaaagac cttcaagcac    480
tgcgacctgg acaacagcgg caagctggac gtggacgaga tgaccagaca gcacctgggc    540
ttctggtaca tcctggaccc caacgccgac ggcctgtacg gcaacttcgt gccttgataa    600
```

<210> SEQ ID NO 15
<211> LENGTH: 600
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 15

```
atggccgaca ccgccagcaa gtacgccgtg aagctgaggc ccaacttcga caaccccaag     60
tgggtgaacc ggcacaagtt catgttcaac ttcctggaca tcaacggcga cggcaagatc    120
accctggacg agatcgtgag caaggccagc gacgacatct gcgccaagct gggcgccacc    180
cccgagcaga ccaagagaca ccaggacgcc gtggaggcct tcttcaagaa gatcggcatg    240
gacttcggca aggaggtgga gttccccgcc ttcgtggacg gctggaagga gctggccaac    300
tacgacctga agctgtggag ccagaacaat aagagcctca tcagggactg gggcgaggcc    360
gtgttcgaca tcctcgacaa ggacggcagc ggcagcatca gcctggatga gtggaaggcc    420
tacggcagaa tcagcggcat ctgcagaagc gacgaggacg ccgaaaagac cttcaagcac    480
tgcgacctgg acaacagcgg caagctggac gtggacgaga tgaccagaca gcacctgggc    540
ttctggtaca ccctggaccc caacgccgac ggcctgtacg gcaacttcgt gccttgataa    600
```

<210> SEQ ID NO 16
<211> LENGTH: 600
<212> TYPE: DNA
<213> ORGANISM: Artificial Sequence
<220> FEATURE:

<223> OTHER INFORMATION: Description of Artificial Sequence: Synthetic
    nucleotide construct

<400> SEQUENCE: 16

```
atggccgaca ccgccagcaa gtacgccgtg aagctgaggc ccaacttcga caaccccaag        60
tgggtgaacc ggcacaagtt catgttcaac ttcctggaca tcaacggcga cggcaagatc       120
accctggacg agatcgtgag caaggccagc gacgacatct gcgccaagct gggcgccacc       180
cccgagcaga ccaagagaca ccaggacgcc gtggaggcct tcttcaagaa gatcggcatg       240
gactacggca aggaggtgga gttccccgcc ttcgtggacg gctggaagga gctggccaac       300
tacgacctga agctgtggag ccagaacaag aagagcctca tcagggactg gggcgaggcc       360
gtgttcgaca tcttcgacaa ggacggcagc ggcagcatca gcctggatga gtggaaggcc       420
tactgcagaa tcagcggcat ctgcagcagc gacgaggacg ccgaaaagac cttcaagcac       480
tgcgacctgg acaacagcgg caagctggac gtggacgaga tgaccagaca gcacctgggc       540
ttctggtaca ccctggaccc caacgccgac ggcctgtacg caacttcgt gccttgataa        600
```

<210> SEQ ID NO 17
<211> LENGTH: 600
<212> TYPE: DNA
<213> ORGANISM: Artificial Sequence
<220> FEATURE:
<223> OTHER INFORMATION: Description of Artificial Sequence: Synthetic
    nucleotide construct

<400> SEQUENCE: 17

```
atggccgaca ccgccagcaa gtacgccgtg aagctgaggc ccaacttcga caaccccaag        60
tgggtgaacc ggcacaagtt catgttcaac ttcctggaca tcaacggcga cggcaagatc       120
accctggacg agatcgtgag caaggccagc gacgacgtct gcgccaagct gggcgccacc       180
cccgagcaga ccaagagaca ccaggacgcc gtggaggcct tcttcaagaa gatcggcatg       240
gactacggca aggaggtgga gttccccgcc ttcgtggacg gctggaagga gctggccaac       300
tacgacctga agctgtggag ccaaaacaag aagagcctca tcagggactg gggcgaggcc       360
gtgttcgaca tcttcgacaa ggacggcagc ggcagcatca gcctggacga gtggaaggcc       420
tacggcagaa tcagcggcat ctgcagaagc gacgaggacg ccgaaaagac cttcaagcac       480
tgcgacctgg acaacagcgg caagctggac gtggacgaga tgaccagaca gcacctgggc       540
ttctggtaca ccctggaccc caacgccgac ggcctgtacg caacttcgt gccttgataa        600
```

<210> SEQ ID NO 18
<211> LENGTH: 600
<212> TYPE: DNA
<213> ORGANISM: Artificial Sequence
<220> FEATURE:
<223> OTHER INFORMATION: Description of Artificial Sequence: Synthetic
    nucleotide construct

<400> SEQUENCE: 18

```
atggccgaca ccgccagcaa gtacgccgtg aagctgaggc ccaacttcga cgaccccaag        60
tgggtgaacc ggcacaagtt catgttcaac ttcctggaca tcaacggcga cggcaaggtc       120
accctggacg agatcgtgag caaggccagc gacgacatct gcgccaggct gggcgccacc       180
cccgagcaga ccaagagaca ccaggacgcc gtggaggcct tcttcaagaa gatcggcatg       240
gactacggca agaggtgga gttccccgcc ttcgtggacg gctggaagga gctggccaac       300
tacgacctga agctgtggag ccagaacaag aagagcctca tcagggactg gggcgaggcc       360
gtgttcgaca tcttcgacaa ggacggcagc ggcagcatca gcctggatga gtggaaggcc       420
```

-continued tacggcagaa tcagcggcat ctgcagcagc gacgaggacg ccgaaaagac cttcaagcac     480
tgcgacctgg acaacagcgg caagctggac gtggacgaga tgaccagaca gcacctgggc     540
ttctggtaca ccctggaccc caacgccgac ggcctgtacg caacttcgt gccttgataa     600

<210> SEQ ID NO 19
<211> LENGTH: 597
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 19
atggccgaca ccgccagcaa gtacgccgtg aagctgcggc ccaacttcga caaccccaag     60
tgggtgaacc ggcacaagtt catgttcaac ttcctggaca tcaacggcga cggcaagatc    120
accctggacg agatcgtgag caaggccagc gacgacatct cgccaagct ggaggccacc    180 cccgagcaga ccaagcggca ccaagtgtgc gtggaggcct tcttccgcgg ctgcggcatg    240
gagtacggca aggagatcgc cttcccccag ttcctggacg gctggaagca gctggccaca    300
agcgagctga agaagtgggc ccggaacgag cccaccctga tccgcgagtg gggcgacgcc    360
gtgttcgaca tcttcgacaa ggacggcagc ggcagcatct ctctggacga gtggaaggcc    420
tacggccgga tcagcggcat ctgcagcagc gacgaggacg ccgagaaaac cttcaagcac    480
tgcgacctgg acaacagcgg caagctggac gtggacgaga tgacccggca gcacctgggc    540
ttctggtaca ccctggaccc caacgccgac ggcctgtacg caacttcgt gccctga       597

<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gatgacgacg acaagatggc cgacaccgcc ag                                   32

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gaggagaagc ccggtttatc aaggacacga agt                                  33

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tcgttgggat ccgccaccat ggccgacacc gcc                                  33

<210> SEQ ID NO 23
<211> LENGTH: 27

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gggccctcta gattatcaag gcacgaa                                              27

<210> SEQ ID NO 24
<211> LENGTH: 99
<212> TYPE: DNA
<213> ORGANISM: Homo sapiens

<400> SEQUENCE: 24
atgtccgtcc tgacgccgct gctgctgcgg ggcttgacag gctcggcccg gcggctccca         60
gtgccgcgcg ccaagatcca ttcgttggga tccgccacc                                99
```

PHOTOPROTEINS WITH ENHANCED BIOLUMINESCENCE AND ASSAYS USING THE SAME

CROSS-REFERENCE TO RELATED APPLICATION

This application is a National Stage entry of International Application No. PCT/EP2006/002172, filed Mar. 9, 2006, the entire specification claims and drawings of which are incorporated herewith by reference.

The present invention relates to photoproteins with enhanced bioluminescence and to their use as intracellular calcium indicators. The photoproteins are obtained by mutagenesis of the clytin coding sequence and show enhanced bioluminescence, high affinity for calcium and long-lasting light emission. They are conveniently used in cell-based assays to determine variations of intracellular calcium concentration, particularly in assays for the screening of molecules with high and ultra-high-throughput techniques.

BACKGROUND OF THE INVENTION

Bioluminescence is the phenomenon by which visible light is emitted by living organisms or by a substance derived from them through a variety of chemiluminescent reaction systems. Bioluminescence reactions require three major components: a luciferin, a luciferase and molecular oxygen. However, other components may also be required in some reactions, including cations ($Ca^{++}$ and $Mg^{++}$) and cofactors (ATP, NAD(P)H). Luciferases are enzymes that catalyse the oxidation of a substrate, luciferin, and produce an unstable intermediate. Light is emitted when the unstable intermediate decays to its ground state, generating oxyluciferin. There are many different unrelated types of luciferin, although many species from at least seven phyla use the same luciferin, known as coelenterazine. In some animals (e.g. jellyfish) the luciferin/luciferase system can be extracted in the form of a stable "photoprotein" which emits light upon calcium binding. Photoproteins differ from luciferases in that they are stabilized oxygenated intermediate complexes of luciferase and luciferin. Photoproteins are present in many marine coelenterates and allow these organisms to emit light for a variety of purposes including breeding, feeding and defense (1). There are many luminescent organisms, but only seven photoproteins, namely Thalassicolin (2,3), Aequorin (4-6), Mitrocomin (syn. with Halistaurin) (7,8), Clytin (syn. with Phialidin) (8,9), Obelin (2,6,10,11), Mnemiopsin (12,13) and Berovin (12,13) have been isolated so far. All these proteins are complexes formed by an apoprotein, an imidazopyrazine chromophore (coelenterazine) and oxygen. Their structures are highly conserved, especially in the region containing the three calcium binding sites (EF-hand structures). The term "photoprotein" identifies the luciferin-bound polypeptide, which is capable of luminescence, while "apophotoprotein" is used to indicate the protein without luciferin.

The most studied photoproteins are Aequorin, isolated from *Aequorea victoria* (14) and Obelin, isolated from *Obelia longissima* (15). The photoprotein may be regenerated from the apophotoprotein by incubation with coelenterazine, molecular oxygen, EDTA and 2-mercaptoethanol or dithiothreitol. Since coelenterazine is the common luminescent substrate used by the photoproteins Aequorin, Mitrocomin, Clytin and Obelin, the light-emitting reaction is likely the same in these four photoproteins (16,17).

The Clytin photoprotein was cloned in 1993 by Inouye et al. (18). To date not much work has been done on this photoprotein. The primary structures of aequorin, mitrocomin, clytin and obelin were aligned and showed very strong amino acid sequence identities. The $Ca^{2+}$-binding sites of Clytin were also found to be highly conserved (19). It was found that hydrozoan $Ca^{2+}$-binding photoprotein differs from other $Ca^{2+}$-binding proteins such as calmodulin and troponin C by a relatively high content of cysteine, histidine, tryptophan, proline and tyrosine residues.

The analysis of the primary structure of clytin shows that it contains 198 aminoacidic residues (aa) and belongs to the family of photoproteins.

Photoproteins are widely used in reporter gene technology to monitor the cellular events associated with signal transduction and gene expression.

The study of cellular events and their regulation requires sensitive, non invasive analytic methods. Photoproteins and in general the use of bioluminescence are excellent reporter systems as they have virtually no background in contrast to fluorescence systems.

Photoproteins are expressed in mammalian cells to monitor calcium changes in response to different stimuli. Intracellular calcium concentrations can be measured by adding the cofactor coelenterazine to mammalian cells expressing the photoprotein and detecting photon emission, which is indicative of intracellular calcium concentration. The use of cells which express both a photoprotein and a receptor involved in the modulation of intracellular calcium concentration provides a valid system for the screening of compounds for their effects on the release of intracellular calcium. High throughput screening assays can also be designed using a photoprotein as reporter system. The sensitivity of the system as well as its high signal to noise ratio allow the use of small assay-volumes. Aequorin is up to now the most used photoprotein for these screening assays.

Calcium flux assays are commonly carried out in HTS format utilizing optical screening apparatuses suited for the simultaneous analysis of a high number of samples and equipped with a luminescence imaging system with a CCD Camera detector. However, one of the most used instruments in HTS is FLIPR® (Fluorometric Imaging Plate Reader, Molecular Devices Corporation, Sunnyvale, Calif., USA) which was developed as a high throughput optical screening tool for cell-based fluorescent assays. The apparatus is equipped with an optical detection device that allows for signal isolation on a cell-monolayer, thereby enhancing sensitivity for cell-based assays. The excitation source can be either an Argon laser or a broadband source as a Xenon lamp.

With a light-tight enclosure, extremely sensitive and fast camera, and true simultaneous on-line liquid dispensing, the FLIPR® system most recent versions (FLIPR$^3$ and FLIPR$^{TETRA}$) have been made suitable also for luminescence assays, even if with lower sensitivity compared to CCD Camera-based equipments.

For the use of the above described instruments FLIPR®, FLIPR$^3$ and FLIPR$^{TETRA}$ and in general for all instruments with a low sensitivity for luminescence assays, a photoprotein with enhanced light emission is highly desirable.

DISCLOSURE OF THE INVENTION

According to a first aspect, the invention provides an isolated photoprotein containing an amino acid sequence which:
 a) is able to bind coelenterazine and calcium, producing bioluminescence;
 b) has an identity of at least 90%, preferably of at least 95%, more preferably of at least 98% to SEQ ID NO: 1 (Clytin);

c) in sequence alignment with SEQ ID NO: 1 (Clytin), presents one of the following single or multiple substitutions (the residue positions are referred to SEQ ID NO: 1):
  i) $C_{54} \rightarrow S$;
  ii) $S_{132} \rightarrow C$;
  iii) $K_{48} \rightarrow R$, $N_{195} \rightarrow D$;
  iv) $Q_{68} \rightarrow R$, $A_{90} \rightarrow V$, $T_{184} \rightarrow I$;
  v) $Y_{82} \rightarrow F$, $K_{110} \rightarrow N$, $F_{125} \rightarrow L$, $S_{149} \rightarrow R$;
  vi) $G_{142} \rightarrow C$;
  vii) $I_{53} \rightarrow V$, $S_{149} \rightarrow R$;
  viii) $N_{18} \rightarrow D$, $I_{40} \rightarrow V$, $K_{56} \rightarrow R$
  ix) $Gly_{58} \rightarrow Glu$, $Asp_{69} \rightarrow Val$, $Ala_{70} \rightarrow Cys$, $Lys_{76} \rightarrow Arg$, $Lys_{77} \rightarrow Gly$, $Ile_{78} \rightarrow Cys$, $Asp_{81} \rightarrow Glu$, $Val_{86} \rightarrow Ile$, $Glu_{87} \rightarrow Ala$, $Ala_{90} \rightarrow Gln$, $Val_{92} \rightarrow Leu$, and $Glu_{97} \rightarrow Gln$ In a preferred embodiment, the photoprotein contains an amino acid sequence which is selected from the group of SEQ ID NO: 2, 3, 4, 5, 6, 7, 8, 9 and 10. Compared to known or commercially available photoproteins, the photoproteins of the invention show improved bioluminescence activity, and/or higher affinity to calcium and/or longer-lasting light emission.

Apart from the indicated residue-substitutions, which confer the desired photoprotein bioluminescence activity, the Clytin sequence can be further modified without negatively affecting the photoprotein's bioluminescence activity, especially by conservative substitutions of amino acidic residues, within the indicated sequence-identity limits. In addition, the Clytin sequence can be deleted of small portions, without altering its photoprotein activity.

In a further aspect, the invention is directed to a polynucleotide encoding a photoprotein as defined above. In a preferred embodiment, the polynucleotide sequences are optimized for mammalian codon usage according to SEQ ID NO: 11, 12, 13, 14, 15, 16, 17, 18, 19. In a further preferred embodiment, the nucleic acid molecules are fused to mitochondrial target sequences (20, 21, 22).

According to a further aspect, the invention provides expression vectors and host cells containing the indicated polynucleotides. Host cells expressing a photoprotein according to the invention produce an intense bioluminescence in response to calcium stimulation, which is much higher than that observed with natural photoproteins, in particular with the most used one, Aequorin.

In a further aspect, the invention provides a cell-based assay for determining intracellular calcium concentration by means of a photoprotein according to the invention.

In a preferred embodiment, the changes in intracellular calcium concentration are determined by:
  a) providing a cell expressing a photoprotein of SEQ ID NO: 2-10, variants or fragments thereof;
  b) loading of the cells with coelenterazine;
  c) contacting the cells with an agent stimulating calcium influx or calcium release from intracellular stores;
  d) detecting the photoprotein's bioluminescence.

The assay is preferably carried out in a high-throughput format utilizing an optical screening tool or apparatus suited for multi-sample analysis, such as a luminescence imaging system with a CCD Camera detector for high and ultra high throughput applications, or with the Fluorometric Imaging Plate Reader (FLIPR®). With both these systems, the photoproteins of the invention produce the highest signal compared to known photoproteins commonly used in automatized cell functional assays.

In a preferred embodiment, cells expressing a photoprotein and a receptor involved in intracellular calcium mobilization are used to test candidate molecules for their effects on receptor modulation. Typically, cells are transfected with an expression vector containing a photoprotein encoding sequence and when not endogenously present, a receptor or channel of interest. The positive clones are selected and plated in a suitable medium, cultured cells are loaded with the coelenterazine substrate and the assay is started by adding the test molecule or stimulus. The produced luminescence is read by a suitable detection system (CCD camera or luminometer). The assay can also be run in an automatic apparatus equipped with multi-well plate reading, in particular the FLIPR® system. In this case, photoprotein-expressing cells are plated in microplate wells, which, after addition of the test molecule/stimulus, are read simultaneously with signal recording.

High throughput screening assays set up with a photoprotein-based reporter system show improved sensitivity and signal-to-noise ratio. Cells expressing a photoprotein of the invention produce an intense bioluminescence in response to calcium stimulation, which is generally higher than that observed with natural photoproteins.

In a further aspect, the invention provides an assay kit containing a preparation of cells expressing an invention photoprotein under the control of a stable or inducible promoter, and reagents suitable for running the assay.

In addition, the photoproteins of the invention may be used as intracellular calcium indicators in diagnostic methods based on the measurement of cellular calcium ion concentration and/or cellular calcium ion influx/outflow.

The invention will be described in more detail in the following experimental section.

Materials and Methods

Reagents

Restriction enzymes were purchased from New England Biolabs and used according to supplier's instructions. The Ligation Independent Cloning (LIC) kit was from Novagen (Nottingham, UK). For in vitro Transcription and Translation we used the TNT Quick coupled kit from Promega (Madison, Wis.). Reagents for PCR, and competent cells of *E. coli* strains XL-1Blue and BL21-Gold(DE3), were from Stratagene (La Jolla, Calif.). Oligonucleotides were purchased from Primm (Milan). Coelenterazine was from Pharma Tech. International Inc. (Fairfield, N.J.). All other chemicals were from standard sources and were of reagent grade or better.

1. Generation of a Randomly Mutagenized Library and Screening 1.1 Photoprotein Optimization for Expression in Mammalian Cells (Geneart Gmbh, Regensburg, Germany)

The codon usage of the wild-type clytin gene was adapted to the codon bias of highly expressed mammalian genes. In addition regions of very high (>80%) or very low (<30%) GC content have been avoided where possible.

For efficient translation initiation the Kozak-consensus sequence was introduced upstream of the start codon. Two STOP codons were added to ensure efficient termination.

1.2 Random Mutagenesis

The GeneMorph II Random Mutagenesis kit (Stratagene) was used following supplier's instructions. Two different initial amounts of target DNA were used to achieve a high mutation rate, 0.1 ng and 0.01 ng.

PCR primers were appropriately designed to contain 5' LIC extensions (in italics) corresponding to sequences described in the Ek/LIC Cloning Kit (Novagen)

```
Upper:
GATGACGACGACAAG-ATGGCCGACACCGCCAG   (SEQ ID NO: 20)

Lower:
GAGGAGAAGCCCGGT-TTATCAAGGACACGAAGT  (SEQ ID NO: 21)
```

Amplification protocol performed in the Perkin Elmer 2400 thermocycler:

1 time the following step:

| pre PCR | 2' at 94° C. |
|---|---|
| 30 times the following steps: | |
| denaturation | 30" at 94° C. |
| annealing | 30" at 56° C. |
| elongation | 40" at 72° C. |
| 1 time the following step: | |
| elongation | 10' at 72° C. |

Expected length of specific PCR product: 630 bp.

To quantitatively determine the amount of DNA obtained, amplification products were analysed by electrophoresis on 1% agarose gel in 1×TAE running buffer following standard procedure, as described by Maniatis et al. The samples were compared to a DNA molecular weight marker (MWXVI, Roche).

1.3 Ek/LIC Cloning

The Novagen Ligation Independent Cloning (LIC) kit was used following suppliers instructions in order to obtain directional cloning of the PCR products without the need of restriction enzyme digestion or ligation reactions. The pET-30 Ek/LIC vector, engineered to express the target protein immediately downstream of an enterokinase cleavage site, was chosen.

1.4 Transformation

For good protein expression we chose BL21-Gold(DE3) cells (Stratagene), a derivative of $E.\ coli$ B, an improved strain of BL21 competent cells. The genotype of the strain is: $E.\ coli$ B F$^-$ ompT hsdS ($r_B^-m_B^-$) dcm$^+$ Tet$^r$ gal λ(DE3) endA Hte. This strain lacks both the ion and the ompT proteases, which can degrade proteins during purification. Hte phenotype increases the transformation efficiency (>1×10$^8$ cfu/μg of pUC18 DNA) In addition the endA gene, that encodes endonuclease I is inactivated (no degradation of plasmid DNA).

In order to obtain competent cells with a high efficiency of transformation, we followed the standard protocol for preparing and electro-transforming BL21-Gold(DE3) cells described in the $E.\ coli$ Pulser Transformation apparatus manual (BioRad).

Transformation efficiency was tested by using the pUC18 DNA and the pET DNA vectors and the efficiencies obtained were:

1×10$^{10}$ cfu/μg of pUC18 DNA

1×10$^8$ cfu/μg of pET DNA

Using these highly electrocompetent cells we were able to obtain a library of approximately 84,000 colonies expressing the randomly mutated Clytin photoprotein.

1.5 Plating, Induction and Charging

Transformed cells were plated on an LB agar plates and grown overnight at 37° C. After overnight colony growth, induction was obtained by adding 10 mM IPTG and 5 mM EDTA, and incubating for 4 hours at 37° C. Colonies were charged with 10 μM Coelenterazine solution and incubated overnight at 4° C. in the absence of light.

1.6 CCD Camera Measurement

Bioluminescence is assayed by the detection of the signal over a fixed time period of 30" at time 0, after 3 and after 5 minutes from the first measurement.

1.7 Colony Picking and Re-Testing

The best colonies were picked and grown in 1 ml of LB liquid medium and re-tested using the same experimental conditions described before.

2. In Vitro Transcription and Translation

Translation of the photoproteins was carried out in the rabbit reticulocyte cell-free system (TNT Quick coupled kit, Promega), following the general instructions of the supplier. 500 ng of DNA was used for each in vitro transcription/translation reaction mix. The reaction volume (10 μl) included 8 μl of TNT T7 Quick Master Mix, 1.6 μl of DNA, 0.2 μl of the Methionine buffer and 0.2 μl of Coelenterazine (0.5 mM). To this end, 5 μl from each sample of the translation mixture were tested for light emission by the injection of calcium solution and by measuring at the Ascent Luminoskan (Labsystems).

3. Recombinant Protein Production

For the production of the recombinant protein we followed a small scale protein purification protocol under native conditions. Due to the presence of an N-terminal His tag in our constructs, we decided to purify the expressed proteins on Ni-NTA Spin Columns (Qiagen) following the suppliers' protocol.

4. Calcium Concentration Curve

In order to evaluate the response of the photoprotein to different calcium concentrations, 0.05 ng/well (96 MTP) of the recombinant protein were charged with Coelenterazine 10 μM overnight at 4° C.

After incubation, different concentrations of CaCl$_2$ were injected and the light released was measured at the Ascent Luminoskan with an integration time of 20 ms for a total time of 10 seconds.

5. Expression of the Mutant Photoprotein in Mammalian Cells

Reagents

Restriction enzymes were purchased from New England Biolabs (Beverly, Mass.) and used according to supplier's instructions. Rapid DNA ligation kit and Fugene transfection reagent were purchased from Roche (Basel, CH). Coelenterazine was from Pharma Tech. International Inc. (Fairfield, N.J.). All other chemicals were from standard sources and were of reagent grade or better.

Cloning Procedure

The most promising mutant photoprotein clones were subcloned for testing their expression in mammalian cells.

2 μl of plasmid were used as template in PCR analysis. In addition a negative control was performed with no template.

Standard PCR procedure were as indicated by Perkin Elmer. PCR protocol was as follows:

Primers:

```
Upper primer:
TCGTTGGGATCCGCCACCATGGCCGACACCGCC   (SEQ ID NO: 22)

Lower primer:
GGGCCCTCTAGATTATCAAGGCACGAA         (SEQ ID NO: 23)
```

PCR reaction mix:

| | | |
|---|---|---|
| 2 µl | template | |
| 5 µl | 10× Pfx Buffer (GIBCO-LifeTechnologies) | |
| 1.5 µl | 10 mM dNTPs | |
| 1 µl | 50 mM $MgSO_4$ (GIBCO-LifeTechnologies) | |
| 2.5 µl | upper primer (10 µM) | |
| 2.5 µl | lower primer (10 µM) | |
| 2.5 U | Platinum Pfx (GIBCO-LifeTechnologies) | |
| 35 µl | $H_2O$ | |

Amplification protocol performed in Perkin Elmer 2400 thermocycler:
1 time the following step:

| | |
|---|---|
| pre PCR | 2' at 94° C. |
| 25 times the following steps: | |
| denaturation | 15" at 94° C. |
| annealing | 30" at 56° C. |
| elongation | 40" at 68° C. |
| 1 time the following step: | |
| elongation | 10 ' at 68° C. |

Expected length of specific PCR product: 630 bp.

Amplification products were analysed by electrophoresis on 1% agarose gel in 1xTAE running buffer following the standard procedure, as described by Maniatis et al.

The PCR product was gel purified using Qiagen columns and digested with BamHI and XbaI restriction enzymes.

pcDNA3neo-/mitoMutated-Clytin Construction

An in-house modified pcDNA3 vector (Invitrogen) has been prepared containing the sequence encoding the mitochondrial targeting peptide from subunit VIII of human cytochrome c oxidase (20, 21, 22) so that it could be used in frame at the 5' end of the codon-usage optimized photoprotein gene. The amplification product obtained from the above mentioned PCR has been cloned into this modified pcDNA3 vector lacking the Neomycin resistance gene for expression in mammalian cell lines.

For the mitochondrial targeting the signal sequence is:

(SEQ ID NO: 24)
5'-ATGTCCGTCCTGACGCCGCTGCTGCTGCGGGGCTTGACAGGCTCGGC

CCGGCGGCTCCCAGTGCCGCGCGCCAAGATCCATTCGTTGGGATCCGCCA

CC-3'.

pcDNA3neo-/cytoMutated-Clytin Construction

The Mutated-clytin gene is obtained from the pcrScript/hMutated-clytin vector by digestion with BamHI and XbaI. The pcDNA3neo- is digested with the BamHI and XbaI restriction enzymes, and purified.

The Mutated-clytin gene is then ligated into the pcDNA3neo-vector to obtain pcDNA3neo-CYTO-hMutated-clytin.

Both constructs obtained were verified by full-length dideoxy sequencing.

Cell Culture

Culture medium, seeding and incubation: DMEM/F12 with Glutamax (GIBCO cod. 31331-028), 10% FBS, 1% Pen./Strep. (Invitrogen cod. 15140-122), 25 mM Hepes Buffer Solution (GIBCO cod. 15630-056), 1.0 mM Sodium Pyruvate (GIBCO cod. 11360-039), 1.5 g/L Sodium Bicarbonate (GIBCO cod. 25080-060).

Preculture conditions: Cells were seeded for experiments when 70-80% confluent.

Cell culture conditions: Split twice a week: $3.0 \times 10^5$ cells/flask T75 (recovery: $8 \times 10^6$ cells).

Clone Selection Process:
CHO-K1 were transfected with pcDNA3Neo⁻/MITO-hMutated-clytin or pcDNA3Neo⁻/CYTO-hMutated-clytin.

48 h after transfection, the transfected cells were plated in 10×96 w/p in complete DMEM.

At confluence the 10×96 w/p were duplicated in 10 white plates. 3 ½ hours before measurements, medium was replaced with 50 µl/well of tyrode (2 mM $Ca^{2+}$ and coelenterazine 10 µM).

Positive clones were selected evaluating:
First selection was done lysing cells with TRITON X-100. CCD camera conditions: low sensitivity, integration time 1 second reading for 5 seconds.

Five clones were chosen each diluted in 3×96 w/p.

At confluence the 15×96 w/p were duplicated in 15 white plates. 3½ hours before measurements, medium was replaced with 50 µl/well of tyrode (2 mM $Ca^{2+}$ and coelenterazine 10 µM).

Second selection was done with 10 µM ATP monitoring the kinetics and then cells were lysed with TRITON X-100. CCD camera conditions: low sensitivity, integration time 1 second reading for 30 seconds for the ATP measurement followed by 30 seconds for TRITON X-100.

Four limiting dilutions of the best clone selected were performed, 0.3 cells per well in 10×96 w/p.

The final clone was chosen after the 4th LD selected with ATP 0.25 µM, coelenterazine 5 µM.

Complete optimization of the assay was performed on the best responding clone.

CCD Camera Measurement Parameters:

CHO cells are seeded at different cell densities in 384MTP (500, 750, 1,000, 1,500 cells/well) in growth media supplemented as above and measured with a CCD camera 24 hours and 48 hours after plating. Prior to experiments growth medium is removed and cells are loaded with Tyrode buffer plus coelenterazine at 37° C. for 3 hours. Luminescence is finally monitored by CCD camera after the addition of the agonist (30 sec. kinetic).

Fluorometric Imaging Plate Reader (FLIPR®) Measurements $FLIPR^3$ Settings for Assays Standard Protocol for Luminescence Detection
  384 white wall clear bottom plates
  cell plating 24 hrs before the experiment
  medium removal
  addition of tyrode plus coelenterazine 25 µl/well
  incubation 4 hrs at 37° C.
  experiments run at $FLIPR^3$: compound (2×) injection in tyrode buffer (25 µl/well).

All parameter values are the instrumentation default values, except for the following:
Pre-assay steps:
1) Camera configuration:
  Exposure length=0.7
  Camera gain=200
2) Sequence parameters:
  Dispense 384 well head
  Height=30 µl
  Speed=25 µl/sec
$FLIPR^{TETRA}$ Settings for Assays Standard Protocol for Luminescence Detection
  384 white wall clear bottom plates cell plating 24 hrs before the experiment
medium removal
addition of tyrode plus coelenterazine 25 µl/well
incubation for 4 hrs at 37° C.
experiments run at FLIPR$^{TETRA}$: compound (2×) injection in tyrode buffer (25 µl/well).

All parameter values are the instrumentation default values, except for the following:
Set up read mode:
1) Camera configuration:
Camera Gain=200
Exposure time=0.50
2) Sequence parameters:
Height 30 µl
Speed=25 µl/sec
Reference Compounds:
ATP (Sigma, A-7699) was dissolved in H$_2$O at a concentration of 100 mM and stored in aliquots at −20° C. Working solution was freshly prepared in tyrode buffer.
Tyrode Buffer composition: NaCl 130 mM, KCl 5 mM, CaCl$_2$ 2 mM, MgCl$_2$ 1 mM, NaHCO$_3$ 5 mM e HEPES 20 mM, pH 7.4.
IMETIT (Sigma, I-135)

EXAMPLES

1. Generation of a Randomly Mutagenized Library and Screening

The Random mutant Library was obtained by using the GeneMorph II Random Mutagenesis kit (Stratagene). In order to achieve a high mutation rate two different initial amounts of target DNA were used: 0.1 ng and 0.01 ng. A total of 83305 bacterial colonies were tested for luminescence activity. Of these, 1089 were positive and therefore had bioluminescent characteristics. The best colonies were picked, for a total of 289 colonies, and of these, 16 resulted best after a re-test. Finally 9 colonies were chosen and analysed.

Figure 1:
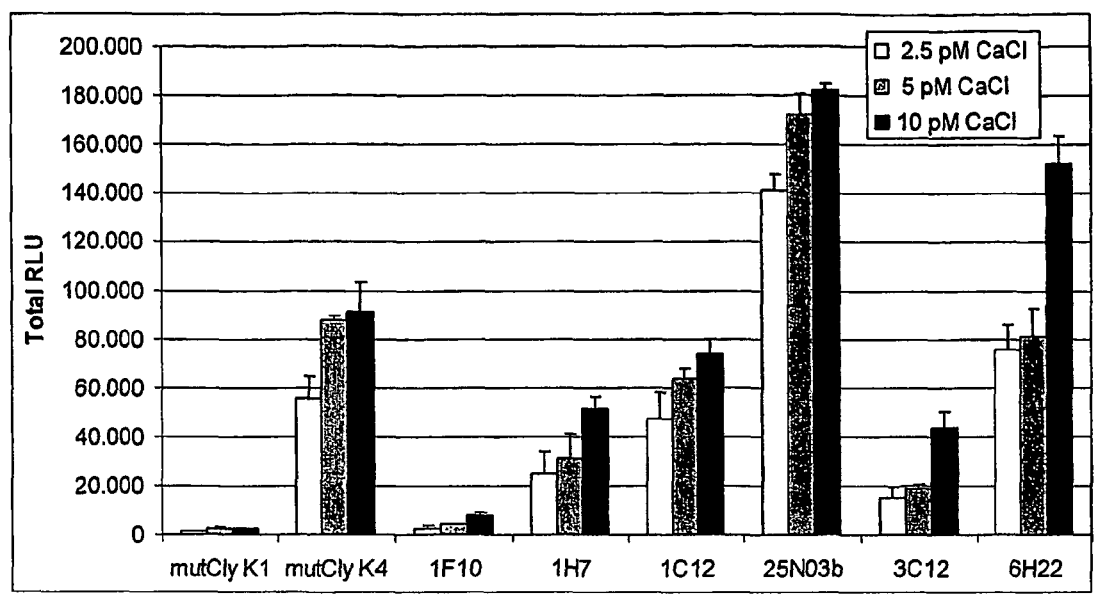
FIG. 1: Re-test of mutant colonies with three calcium concentrations.

FIG. 1 shows the results obtained in a three test-point CaCl$_2$ dose-response curve obtained with the 8 mutants.

2. Photoprotein Assay

5 µl of the translation mixture were directly mixed with 95 µl of PBS solution in a 96 well plate which was mounted into the Luminometer (Berthold). To trigger photoprotein light emission, a 5 µM CaCl$_2$ solution was injected into the well and luminescence recorded for 10 seconds.

Figure 2:
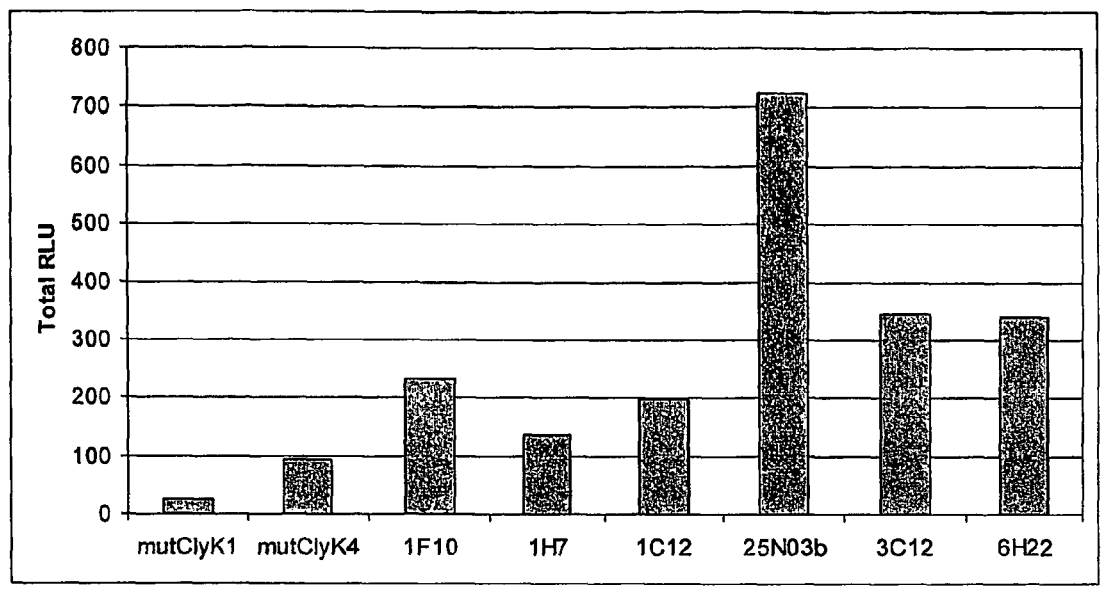
FIG. 2: In vitro Transcription & Translation. Measurement of light emission upon 5 pM calcium injection.

The results of the in vitro transcription and translation of the DNA of the 8 mutants are shown in FIG. 2.

Figure 3:
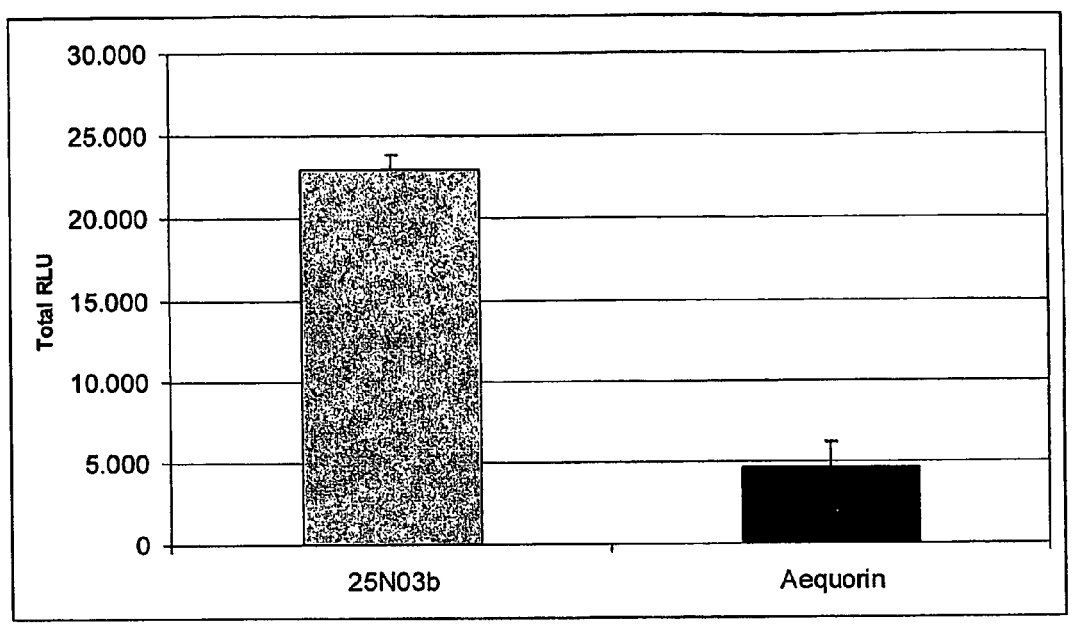
FIG. 3: In vitro Transcription & Translation. Measurement of light emission upon 1 mM calcium injection.

A new in vitro transcription and translation experiment was carried out with the best responding mutant, 25N03b (sequence ID no 16), and with the Aequorin photoprotein (FIG. 3) in order to have a comparison of the light emission upon the injection of 1 mM CaCl$_2$ solution.

3. Recombinant Photoprotein and Calcium Concentration Curve

Figure 4:
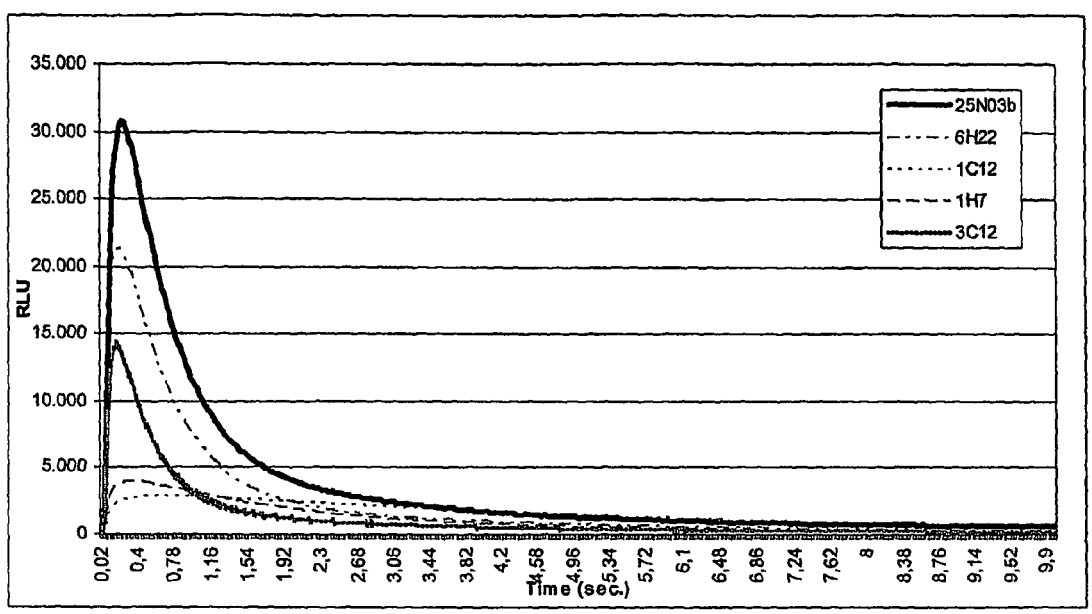
FIG. 4: Kinetics of the measurement of light emission upon 1 mM calcium injection for the recombinant photoproteins.

Recombinant photoproteins corresponding to some mutants were produced under native conditions following a small scale purification protocol. Light emission was measured upon 1 mM calcium injection and the corresponding kinetics are shown in FIG. 4.

Figure 5:
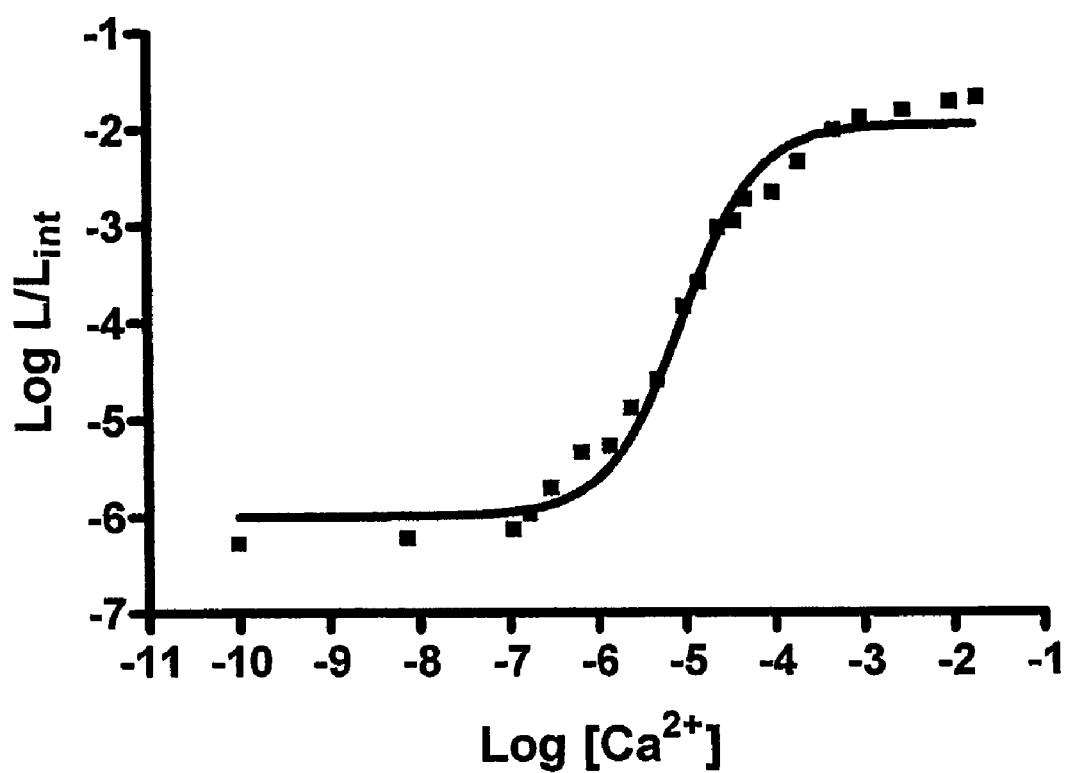
FIG. 5: Calcium dose-response curve of the recombinant photoprotein 25N03b.

The recombinant mutant photoprotein, corresponding to clone 25N03b, was better characterized with a complete calcium dose-response curve, which can be seen in FIG. 5.

Figure 6:
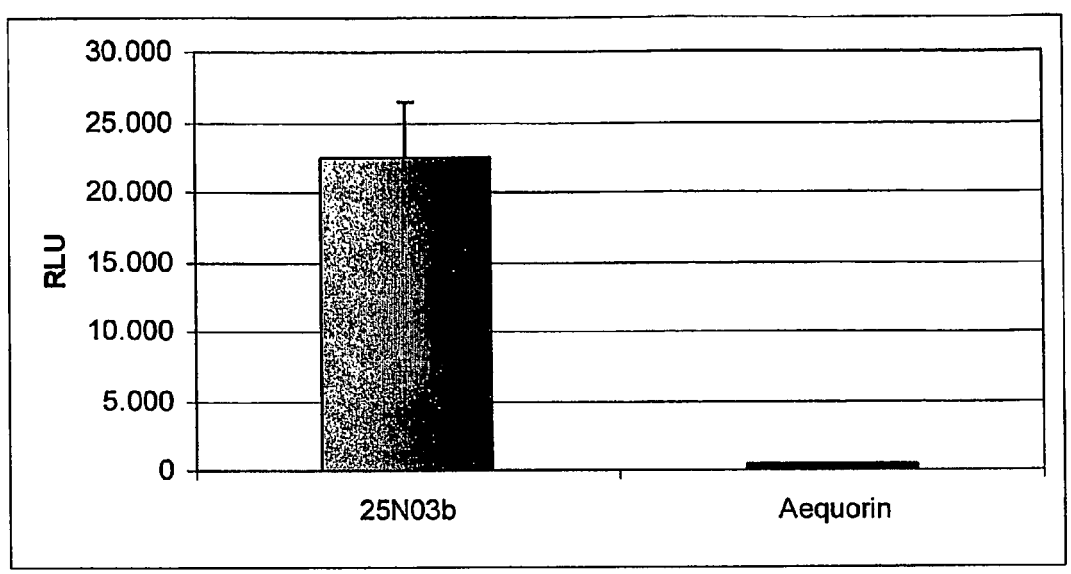
FIG. 6: Peak light intensity from recombinant photoproteins upon 1 mM calcium injection.

In another experiment, the recombinant photoprotein 25N03b was compared to recombinant Aequorin. The light emission recorded upon 1 mM CaCl$_2$ injection was surprisingly higher in the case of the 25N03b mutant as shown in FIG. 6.

Figure 7:
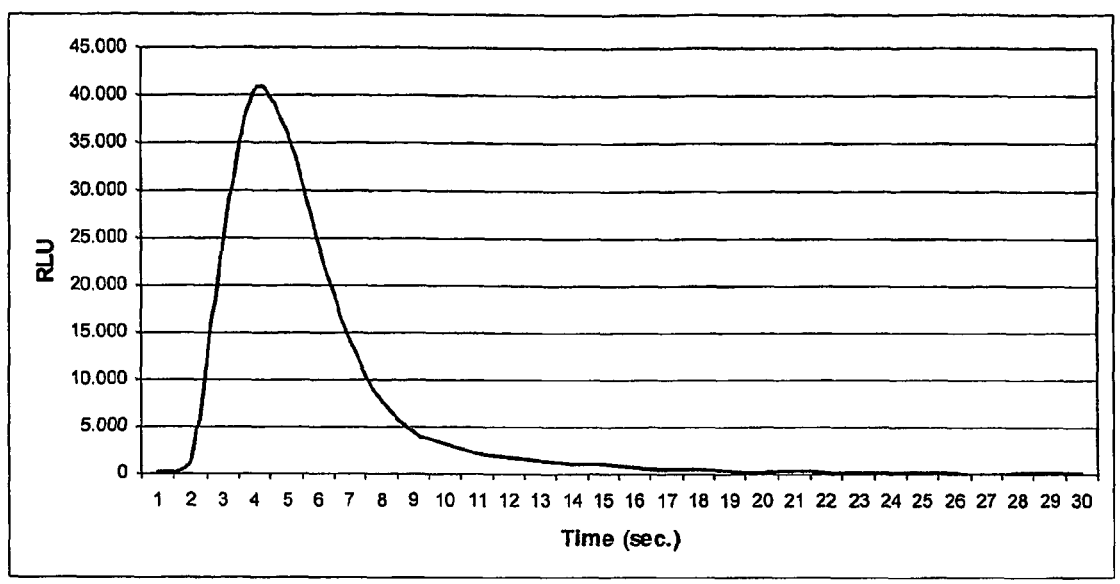
FIG. 7: Kinetics of 10 µM ATP response at the CCD camera for the CHOK1/mito25N03b cell line.

4. Cell-Based Functional Assays 4.1 The CHOmito25N03b-expressing clone (CHOK1/mito25N03b) has been obtained by transfection of CHO-K1 cells (Materials and Methods). 48 hours after transfection the cells were trypsinized and plated into 10×96 MTP (Microtiter Plates) in complete MEM. At confluence, the 10×96 MTP were duplicated using MATRIX (Hudson, N.H., USA) in 10×96 white MTP. 3 hours before measurement the medium was replaced with 50 µl/well of tyrode buffer 2 mM Ca$^{2+}$ and 10 µM coelenterazine. The clones were selected on the basis of their functional response (luminescent signal) to ATP, which is known to stimulate the CHO endogenous receptor P2Y and to rise the cytoplasmic Ca$^{2+}$ concentration. At the end of each experiment, cells were lysed by perfusion of a solution containing Triton X-100. The active photoprotein was reconstituted incubating the cells with 10 µM coelenterazine diluted in tyrode buffer containing 2 mM Ca$^{2+}$, in the dark, at 37° C., in a 5% CO$_2$ atmosphere for 3 hrs. For light emission measurement, cells were lysed in the presence of calcium and the emitted luminescence recorded. The number of photons emitted during the first 30 seconds was integrated by a CCD camera and visualized on the screen. Cells transfected with an empty plasmid or untransfected did not increase photon-emission. To detect changes in calcium concentrations, 10 μM ATP was injected and the kinetics of the response determined. The curve obtained is shown in FIG. 7.

Figure 8:
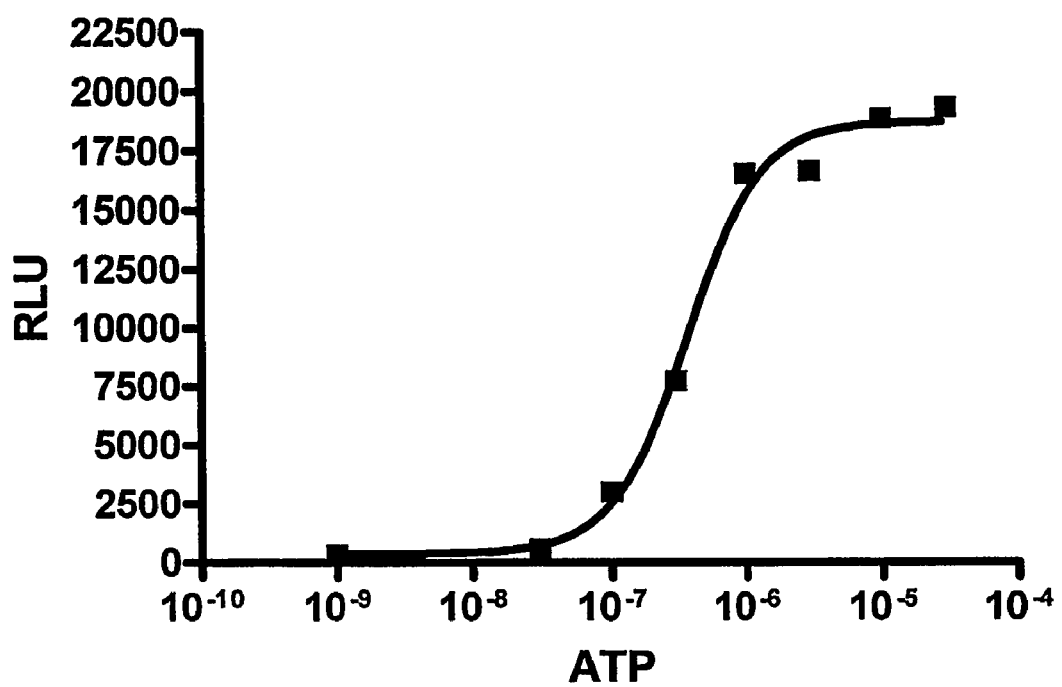
FIG. 8: ATP dose-response curve of the CHOK1/mito25N03b cell line.

The final clone was seeded in 384 w/p and tested with increasing ATP concentrations as shown in the dose-response curve in FIG. 8.

The CHOK1/mito25N03b cell line was also transfected with a G-protein coupled receptor, the Adenosine A3 receptor, and with a chimeric Gα protein, in order to switch the signal to the PLC/IP pathway. A stable cell line was generated (from now on referred as CHOK1/mito25N03b/A3 clone).

Upon stimulation with its agonist, the A3 receptor induces an increase in intracellular calcium concentration which is measured by mito25N03b luminescence.

The final clones of the CHO cell lines expressing mito25N03b and the human Adenosine A3 receptor were grown to 80-95% confluence in tissue culture flasks and harvested by trypsinization. Cells were dispensed at different cell densities in 384 w/p in growth medium (DMEM/F12 containing 10% Foetal Bovine Serum) and incubated for 24 h and 48 h at 37° C. in a humidified incubator at 5% $CO_2$. On the day of the experiment, the culture medium was removed and, for luminescence experiments, cells were loaded with 5 μM coelenterazine for 3 h, at 37° C., 5% $CO_2$. Calcium response was stimulated by addition of different concentrations of ATP to each well. The kinetics of flash luminescence was followed using a CCD camera, which injects reagents and records light emission from each single well.

Figure 14:
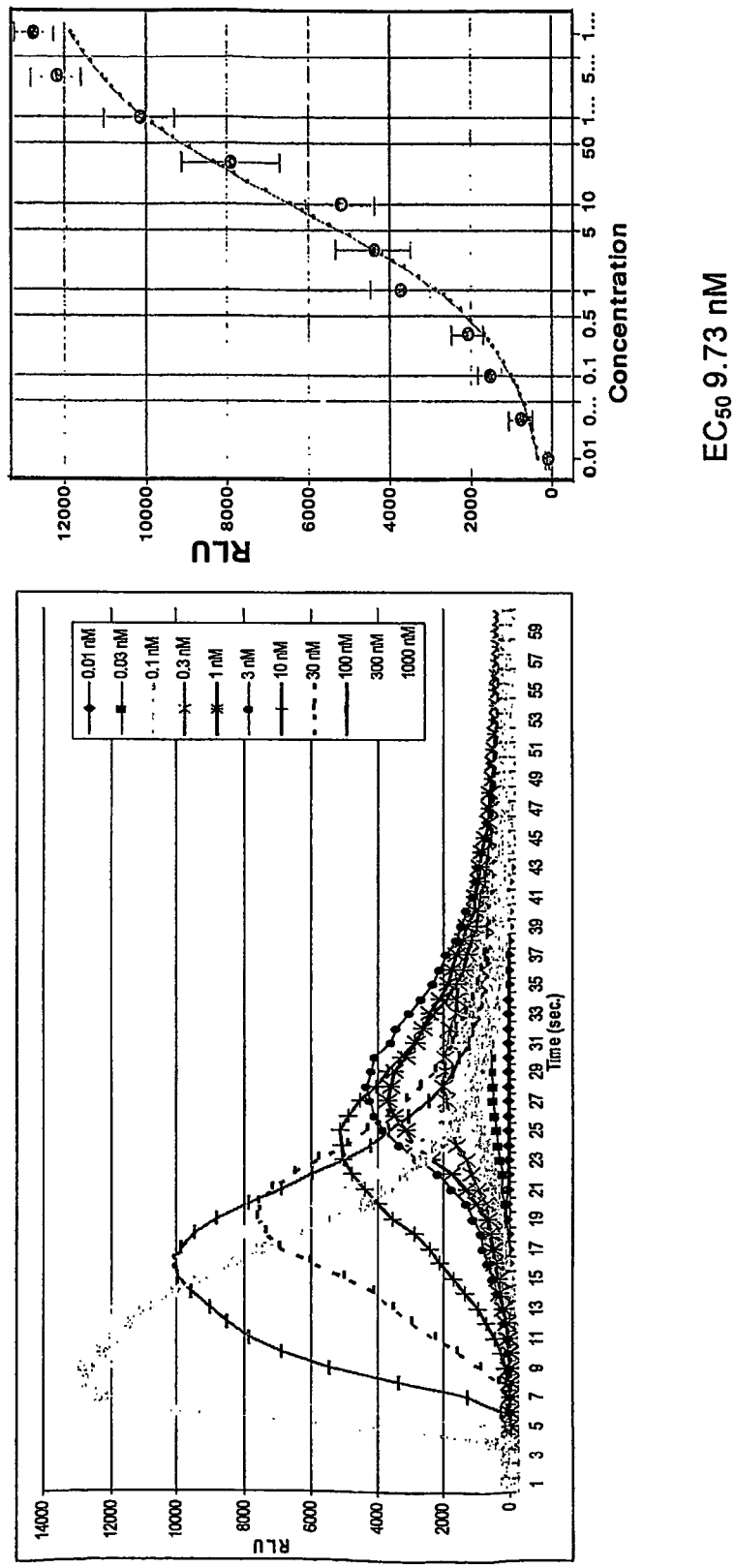
FIG. 14: Dose-response curve of the CHOK1/mito25N03b-A3 cell line with A3 agonist (IB MECA), tested on the Lumibox CCD camera, 500 cells per well, 24 h after seeding. 5 µM coelenterazine. Camera sensitivity 5, 60 second measurement.
Figure 15:
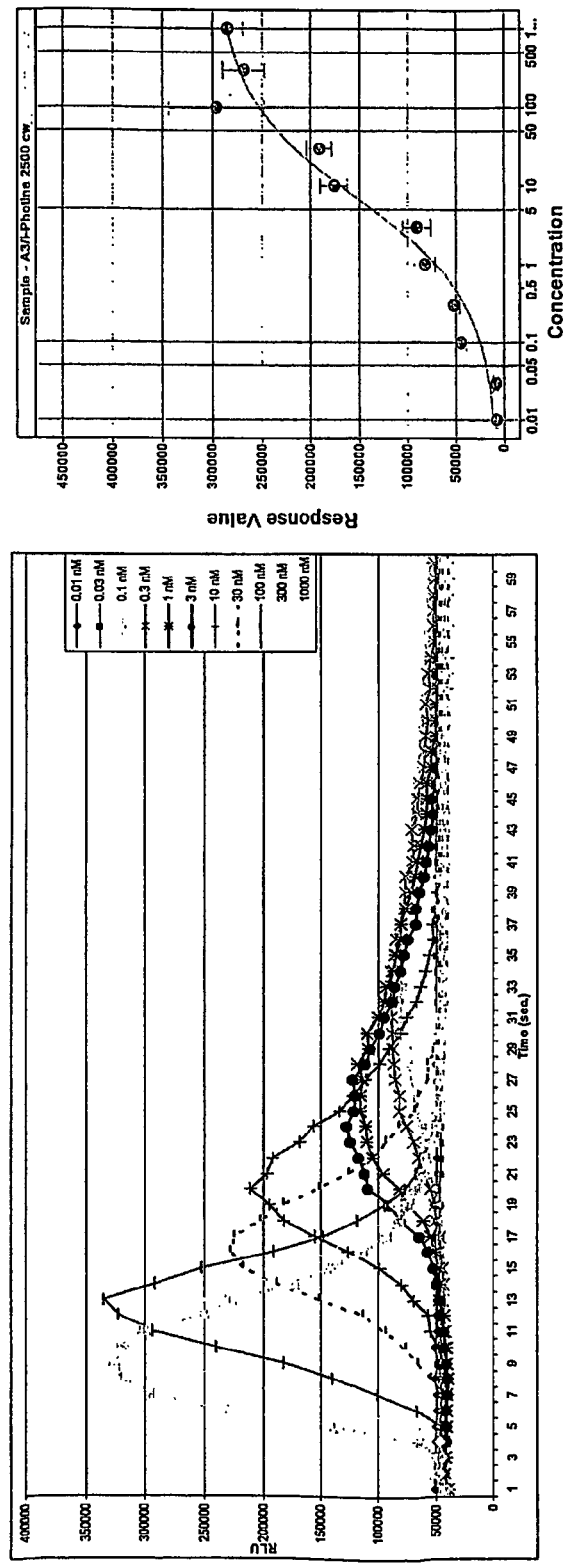
FIG. 15: Dose-response curve of the CHOK1/mito25N03b-A3 cell line with A3 agonist (IB MECA), tested on the CyBi Lumax HT CCD camera, 2500 cells per well, 24 h after seeding. 5 µM CTZ. Camera sensitivity HV 10 analog, 60 second measurement.

The agonist and antagonist were diluted in tyrode buffer at different concentrations. Approximately 25 μl of these solutions were separately injected into each well and the response measured with the CCD camera instrumentation. The emitted light was immediately recorded at different time intervals. Results shown in FIG. 14 refer to the A3 specific agonist, IB-MECA. The same experiments were performed on another CCD camera instrumentation, results are shown in FIG. 15.

4.2 The CHOK1 cells were stably transfected with the mutant 12mutCly (SEQ ID NO: 19) cloned in pcDNA3neo-mito, to obtain the cell line CHOK1/mito12mutCly (Materials and Methods).

Figure 9:
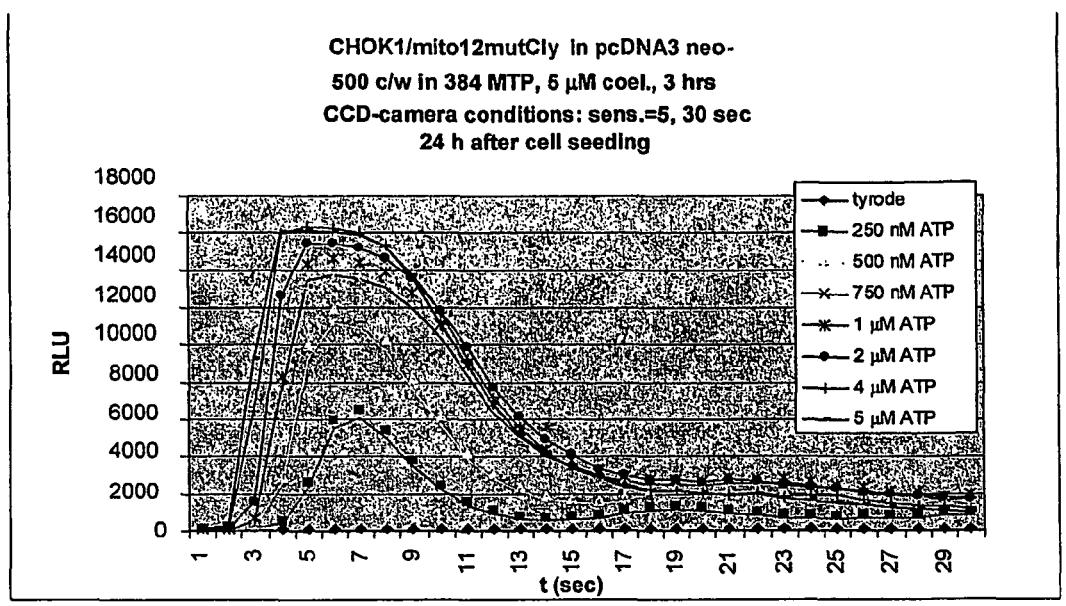
FIG. 9: ATP dose-response kinetic of the CHOK1/mito12mutCly cell line obtained at the CCD camera testing 500 cells/well 24 h after seeding.

The final clone was selected on the basis of the functional response (luminescent signal) to ATP, which is known to stimulate the CHO endogenous receptor P2Y and to rise the cytoplasmic $Ca^{2+}$ concentration. At the end of each experiment, cells were lysed by perfusion of a solution containing Triton X-100. The active photoprotein was reconstituted incubating the cells with 2.5 or 5 μM coelenterazine diluted in tyrode buffer containing 2 mM $Ca^{2+}$, in the dark, at 37° C., in a 5% $CO_2$ atmosphere for 3 hrs. For light emission measurement, cells were lysed in the presence of calcium and the emitted luminescence recorded. The number of photons emitted during the first 30 seconds was integrated by a CCD camera-based luminometer and visualized on the screen. Cells transfected with an empty plasmid or untransfected did not increase photon-emission. Different amount of cells were seeded in 384 MTP. After 24 h to detect changes in calcium concentrations, different ATP concentrations were injected and the kinetics of the response determined. Examples of kinetics obtained seeding 500 cells/well 24 h before the test are shown in FIG. 9.

The high light emission and sensitivity to $Ca^{2+}$ observed in the CHOK1 mito12mutCly cell line allowed the use of a lower number of cells and a lower concentration of coelenterazine even for less time in comparison to the standard-based photoprotein-based cell assays conditions.

Figure 10A:
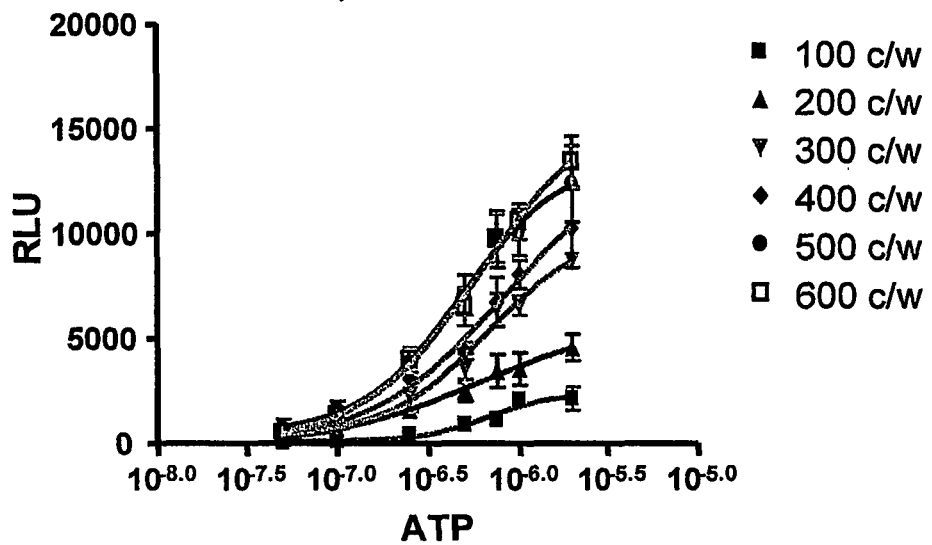
FIG. 10: ATP dose-response curve of the CHOK1/mito12mutCly cell line obtained at the CCD camera with different number of cells/well, different coelenterazine concentrations, and incubation time.
Figure 10B:
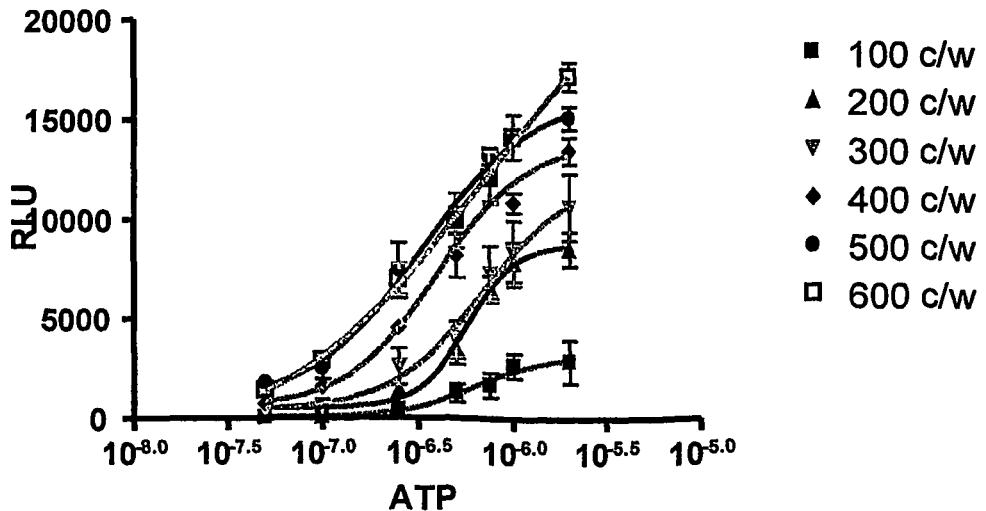

Examples of ATP dose-response curves obtained seeding 100 to 600 cells/well 24 h before the test and incubating the cells with 2.5 and 5 μM coelenterazine diluted in tyrode buffer containing 2 mM $Ca^{2+}$, in the dark, at 37° C., in a 5% $CO_2$ atmosphere for 2 and 3 h are shown in FIG. 10a and 10b.

The CHOK1 cyto12mutCly cell line was obtained by transfection of CHO-K1 cells (Materials and Methods).

Figure 11:
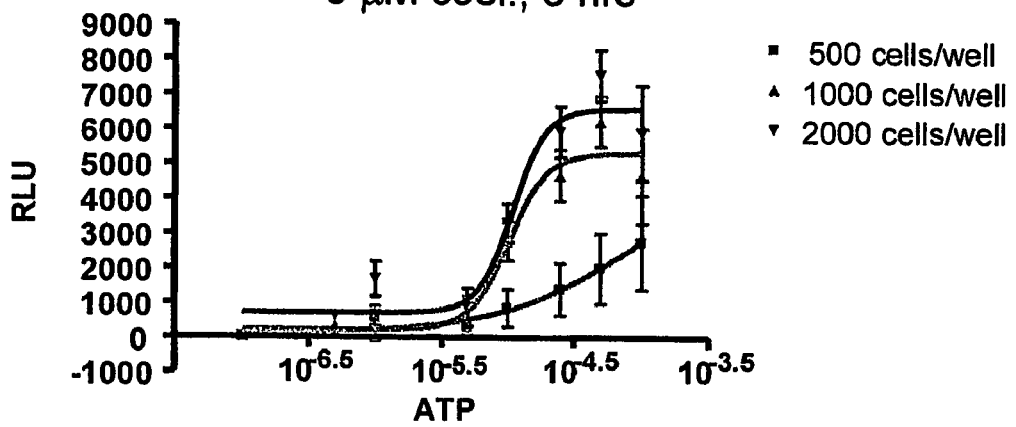
FIG. 11: ATP dose-response curve of the CHOK1/cyto12mutCly cell line obtained at the CCD camera with different number of cells/well.

The final clone was selected on the basis of the functional response (luminescent signal) to ATP, which is known to stimulate the CHO endogenous receptor P2Y and to rise the cytoplasmic $Ca^{2+}$ concentration. At the end of each experiment, cells were lysed by perfusion of a solution containing Triton X-100. The active photoprotein was reconstituted incubating the cells with 2.5 or 5 μM coelenterazine diluted in tyrode buffer containing 2 mM $Ca^{2+}$, in the dark, at 37° C., in a 5% $CO_2$ atmosphere for 3 h. For light emission measurement, cells were lysed in the presence of calcium and the emitted luminescence recorded. The number of photons emitted during the first 30 seconds was integrated by a CCD camera-based luminometer and visualized on the screen. Cells transfected with an empty plasmid or untransfected did not increase photon-emission. Different amount of cells were seeded in 384 MTP. After 24 and 48 h to detect changes in calcium concentrations, different ATP concentrations were injected and the kinetics of the responses determined. ATP dose-response curves obtained seeding 500, 1000 and 2000 cells/well 24 h before the test and incubating the cells with 2.5 and 5 μM coelenterazine diluted in tyrode buffer containing 2 mM $Ca^{2+}$, in the dark, at 37° C., in a 5% $CO_2$ atmosphere for 2 and 3 h are shown in FIG. 11.

The CHOK1 mito12mutCly cell line was transfected with a G-protein coupled receptor, the Histamine-3 receptor, and with a chimeric Gα protein, in order to switch the signal to the PLC/IP pathway. A stable cell line was generated (from now on referred as CHOK1/mito12mutCly/H3 cell line) (Materials and Methods).

Upon stimulation with its agonist (IMETIT), the H3 receptor induces an increase in intracellular calcium concentration which is measured by mito12mutCly luminescence.

Figure 12:
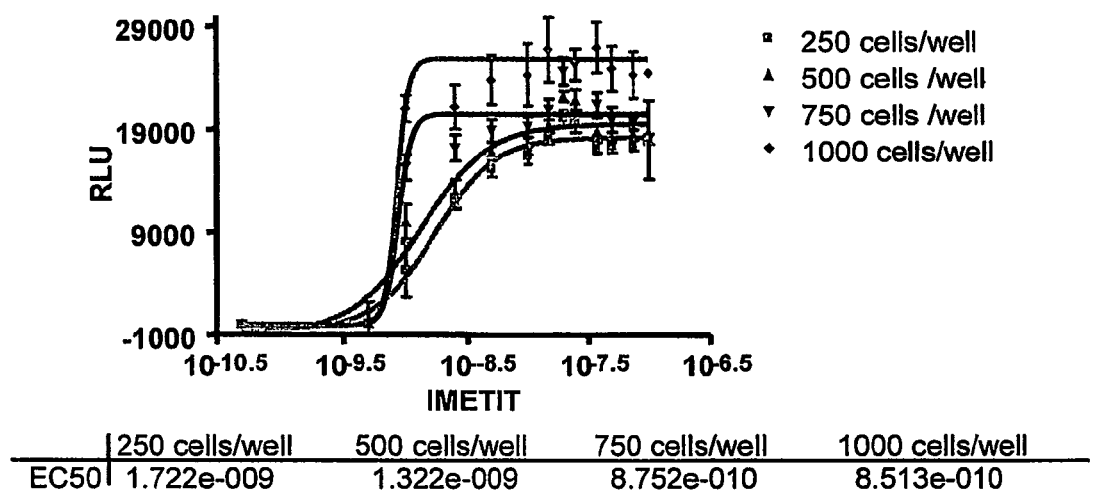
FIG. 12: IMETIT dose-response curve of the CHOK1/mito12mutCly/H3 cell line obtained at the CCD camera with different number of cells/well.

IMETIT dose-response curves obtained seeding 250, 500, 750, and 1000 cells/well 24 h before the test and incubating the cells with 5 μM coelenterazine diluted in tyrode buffer containing 2 mM $Ca^{2+}$, in the dark, at 37° C., in a 5% $CO_2$ atmosphere for 3 h are shown in FIG. 12.

5. Cell-Based Assays at the FLIPR

The CHOK1/mito25N03b/A3 and CHOK1/mito12mutCly/H3 are tested at FLIPR by measuring the luminescence signal induced by the activation of the transfected receptor.

Figure 13:
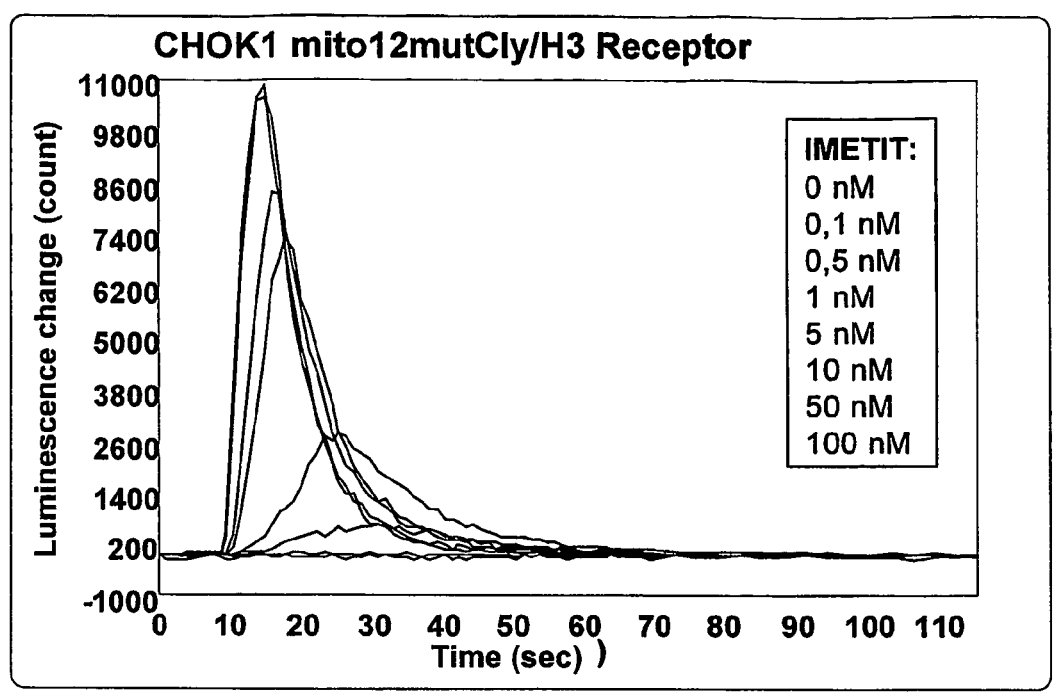
FIG. 13: IMETIT dose-response curve of the CHOK1/mito12mutCly/H3 cell line obtained at FLIPR$^3$.

The luminescence measured with the FLIPR instrumentation is reported as Luminescence Change Units in FIG. 13, wherein are reported the results obtained by measuring the light release induced by IMETIT stimulation on CHOK1/mito12mutCly/H3. 5000 cells/well were seeded in 384 MTP 24 h before the experiment. The medium was replaced and substituted with 25 μl of 2× concentrated coelenterazine (10 μM) diluted in tyrode buffer containing 2 mM $Ca^{2+}$, in the dark, for 3 h at 37° C., in a 5% $CO_2$ atmosphere. IMETIT compound (2×) at different concentrations was injected on cells (25 μl/well).

Figure 16:
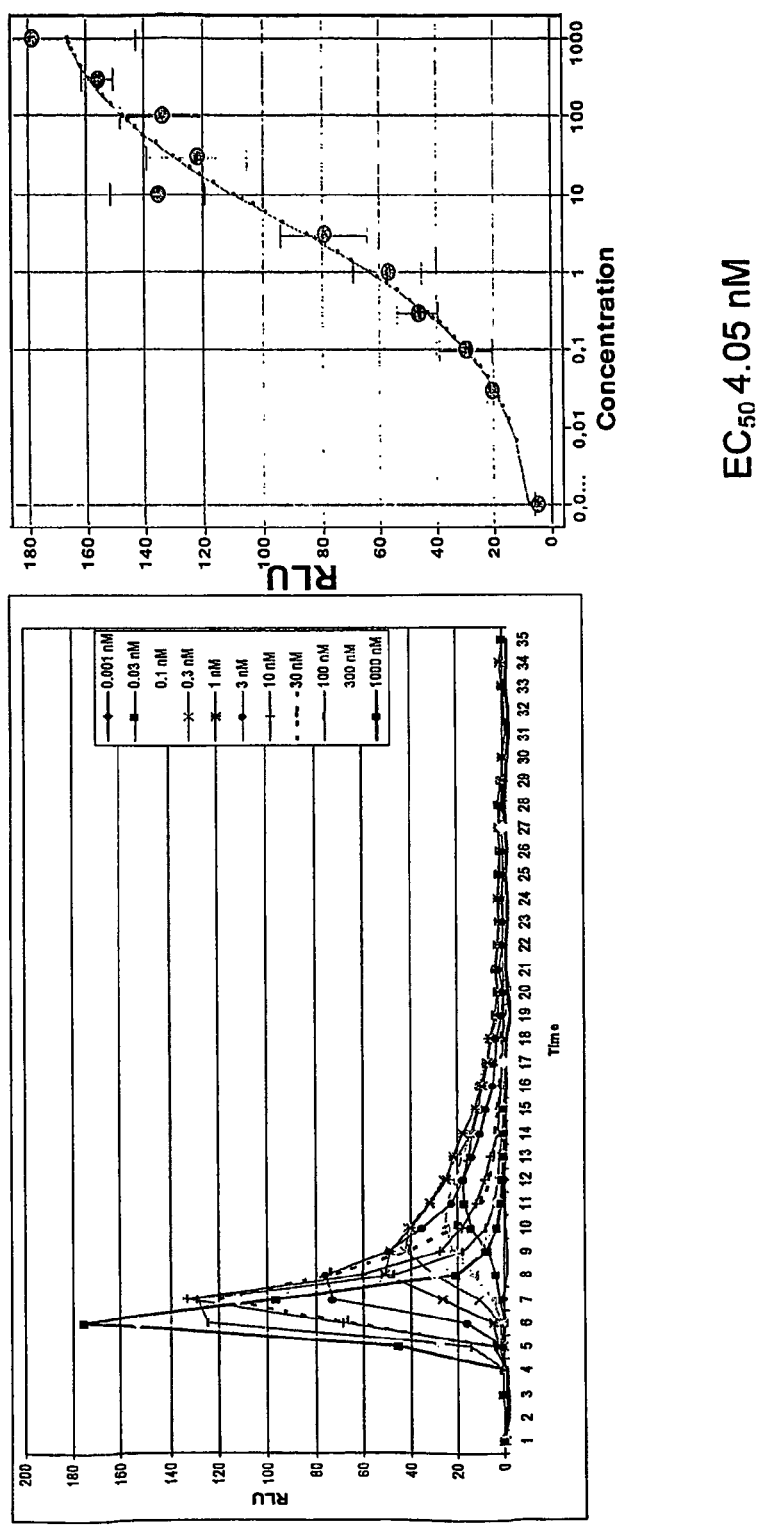
FIG. 16: Dose-response curve of the CHOK1/mito25N03b-A3 cell line with A3 agonist (IB MECA), tested on the FLIPR$^{TETRA}$, 2500 cells per well, 24 h after seeding. 10 µM coelenterazine Exposure time 2 seconds, gain 240.

In FIG. 16 the luminescence measured with the FLIPR$^{TETRA}$ instrumentation is reported as RLU (Relative Light Units), wherein are reported the results obtained by measuring the light release induced by IB-MECA stimulation on CHOK1/mito25N03b/A3. 2500 cells/well were seeded in 384 MTP 24 h before the experiment. The medium was replaced and substituted with 25 µl of 2× concentrated coelenterazine (10 µM) diluted in tyrode buffer containing 2 mM $Ca^{2+}$, in the dark, for 3 h at 37° C., in a 5% $CO_2$ atmosphere. IB-MECA compound (2×) at different concentrations was injected on cells (25 µl/well).

REFERENCES

1. Kendall, J. M., and Badminton, M. N. (1998) *Aequorea victoria* bioluminescence moves into an exciting new era. Trends Biotechnology. 16(5):216-24.
2. Campbell, A. K., Hallet, R. A., Daw, M. E., Ryall, R. C., Hart and Herring P. J. (1981) Application of the photoprotein obelin to the measurement of free $Ca^{++}$ in cells. In Bioluminescence and Chemiluminescence, basic Chemistry and Analytical applications (Edited by M. A. deLuca and W. D. McElroy), pp. 601-607. Academy Press, New York.
3. Herring, P. J. (1979) Some features of the bioluminescence of the radiolarian *Thalassicola* sp. Mar. Biol. 53, 213-216.
4. Shimomura, O., Johnson F. H., and Saiga, Y (1962) Extraction, purification and properties of aequorin, a bioluminescent protein from the luminous hydromedusan, *Aequorea*. J. Cell. Comp. Physiol. 59, 223-239.
5. Shimomura, O., Johnson F. H., and Saiga, Y (1963) Further data on the bioluminescent protein, aequorin. J. Cell. Comp. Physiol. 62, 1-8.
6. Morin, J. G. and Hastings J. W. (1971) Biochemistry of the bioluminescence of colonial hydroids and other coelenterates. J. Cell. Physiol. 77, 305-311.
7. Shimomura, O., Johnson, F. H. and Saiga, Y. (1963) Extraction and properties of halistaurin, a bioluminescent protein from the hydromedusan *Halistaura*. J. Cell. Physiol. 62, 9-15.
8. Shimomura, O., and Shimomura, A. (1985) Halistaurin, phialidin and modified forms of aequorin as $Ca^{++}$ indicator in biological systems. Biochem. J. 228, 745-749.
9. Levine, L. D., and Ward, W. W. (1982) Isolation and characterization of a photoprotein "phialidin" and a spectrally unique green-fluorescent protein from the bioluminescent jellyfish *Phialidium gregarium*. Comp. Biochem. Physiol. 72B, 77-85.
10. Morin, J. G. and Hastings (1971) Energy transfer in a bioluminescent system. J. Cell. Physiol. 77, 313-318.
11. Campbell, A. K. (1974) Extraction, partial purification and properties of obelin the calcium-activated protein from the hydroid *Obelia geniculata*. Biochem. J. 143, 411-418.
12. Ward, W. W. and Selinger (1974) Extraction and purification of calcium-activated photoprotein from the ctenophores *Mnemiopsis* sp. and *Bern ovata*. Biochemistry 13, 1491-1499.
13. Ward, W. W. and Seliger H. H. (1974) Properties of mnemiopsin, and berovin, calcium-activated photoproteins from the ctenophores *Mnemiopsis* sp. and *Beroëovata*. Biochemistry 13, 1500-1510.
14. Johnson, F. H. and Shimomura, O. (1978) Introduction to the bioluminescence of medusae, with special reference to the photoprotein aequorin. Methods Enzymol. 57, 271-291.
15. Illarionov B. A., Bondar V. S., Illarionova V. A., Vysotski E. S. Sequence of the cDNA encoding the $Ca^{++}$-activated photoprotein obelin from the hydroid polyp *Obelia longissima*. Gene. 1995 14; 153(2):273-4.
16. Blinks, J. R., Weir, W. G., Hess, P. and Prendergast, F. G. (1982). Measurement of $Ca^{++}$ concentrations in living cells. Prog. Biophys. Mol. Biol. 40, 1-114.
17. Markova S. V., Vysotski E. S., Blinks J. R., Burakova L. P., Wang B. C., Lee J., (2002) Obelin from the bioluminescent marine hydroid Obelia geniculata: cloning, expression, and comparison of some properties with those of other Ca2+-regulated photoproteins. Biochemistry. 2002 Feb. 19; 41(7):2227-36.
18. Inouye S., Tsuji F. I. (1993) Cloning and sequence analysis of cDNA for the Ca(2+)-activated photoprotein, clytin. FEBS Lett. January 11; 315(3):343-6.
19. Tsuji F. I., Ohmiya Y., Fagan T. F., Toh H., Inouye S. (1995) Molecular evolution of the Ca(2+)-binding photoproteins of the Hydrozoa. Photochem Photobiol. October 62(4):657-61.
20. Rizzuto, R., Simpson, A. W. M., Brini, M. and Pozzan, T. (1992) Rapid changes of mitochondrial Ca2+ revealed by specifically targeted recombinant aequorin. Nature, 358, 325-328.
21. Rizzuto, R., Brini, M., Murgia, M. and Pozzan, T. (1993) Microdomains with high Ca2+ close to IP3-sensitive channels that are sensed by neighbouring mitochondria. Science, 262, 744-747.
22. Rizzuto, R., Bastianutto, C., Brini, M., Murgia, M. and Pozzan, T. (1994) Mitochondrial Ca2+ homeostasis in intact cells. J. Cell Biol., 126, 1183-1194.

---

The invention claimed is:

1. An isolated protein comprising an amino acid sequence wherein:
   a) the protein is able to bind coelenterazine and calcium, producing bioluminescence;
   b) the full-length amino acid sequence of the protein is identical by at least 90% to the full-length amino acid sequence of SEQ ID NO: 1 (Clytin) and;
   c) the amino acid sequence of the protein comprises a $G_{142} \rightarrow C$ substitution (the residue position being with reference to SEQ ID NO: 1).

2. The protein of claim 1, containing an amino acid sequence identical by at least 95% to SEQ ID NO: 1.

3. The protein of claim 2, containing an amino acid sequence identical by at least 98% to SEQ ID NO: 1.

4. The protein according to claim 1, wherein said amino acid sequence is fused to a mitochondrial target sequence.

5. An isolated polynucleotide encoding a photoprotein according to claim 1.

6. The polynucleotide of claim 5, having the sequence of SEQ ID NO: 16.

7. An expression vector containing a polynucleotide according to claim 5.

8. An isolated prokaryotic or eukaryotic host cell containing the vector of claim 7.

9. A host cell according to claim 8 wherein the host cell is a mammalian cell.

10. An in vitro method for detecting changes in intracellular calcium concentration, which comprises:
    a) providing a cell expressing the protein according to claim 1;
    b) allowing the protein to bind with coelenterazine to constitute a photoprotein;
    c) contacting the cell with an agent stimulating calcium influx or calcium release from intracellular stores; and
    d) detecting the photoprotein bioluminescence.

11. A method of screening for compounds modulating intracellular calcium concentration, which comprises:
    a) providing a cell expressing the protein of claim 1;
    b) allowing the protein to bind with coelenterazine to constitute a photoprotein;
    c) contacting the cell with a candidate compound; and
    d) detecting the bioluminescence of the photoprotein.

12. A method according to claim 10, which is carried out in a high-throughput format.

13. A method according to claim 12, which is carried out with a high throughput optical screening apparatus suited for multi-sample analysis.

14. An isolated protein comprising an amino acid sequence set forth in SEQ ID NO: 7.

15. The protein according to claim 14, wherein the amino acid sequence is fused to a mitochondrial target sequence.

16. An isolated composition comprising the protein of claim 1 and coelenterazine.

* * * * *